United States Patent
Mousseau et al.

(10) Patent No.: US 11,436,369 B1
(45) Date of Patent: Sep. 6, 2022

(54) SYSTEMS, DEVICES AND METHODS FOR SECURELY COMMUNICATING WITH ELECTRONIC ASSETS USING AN AUTHENTICATED COMPUTER HUB AND A CENTRAL SERVER

(71) Applicant: 3D BRIDGE SOLUTIONS INC., Vancouver (CA)

(72) Inventors: Gary Mousseau, Waterloo (CA); Karima Bawa, Vancouver (CA)

(73) Assignee: 3D Bridge Solutions Inc., Vancouver (CA)

( * ) Notice: Subject to any disclaimer, the term of this patent is extended or adjusted under 35 U.S.C. 154(b) by 0 days.

(21) Appl. No.: 17/675,723

(22) Filed: Feb. 18, 2022

(51) Int. Cl.
*G06F 21/62* (2013.01)
*G16H 10/60* (2018.01)
*G06F 21/32* (2013.01)
*H04W 4/80* (2018.01)

(52) U.S. Cl.
CPC .......... *G06F 21/6245* (2013.01); *G06F 21/32* (2013.01); *G16H 10/60* (2018.01); *H04W 4/80* (2018.02)

(58) Field of Classification Search
CPC ..... G06F 21/6245; G06F 21/32; G16H 10/60; H04W 4/80
USPC .......................................................... 726/28
See application file for complete search history.

(56) References Cited

U.S. PATENT DOCUMENTS

| | | | |
|---|---|---|---|
| 2016/0165651 A1* | 6/2016 | Pathuri | H04W 8/26 370/329 |
| 2019/0150134 A1* | 5/2019 | Kakinada | H04W 72/048 370/330 |
| 2019/0357023 A1* | 11/2019 | Park | H04W 4/70 |

* cited by examiner

*Primary Examiner* — Jacob Lipman
(74) *Attorney, Agent, or Firm* — Norton Rose Fulbright Canada LLP; Maya Medeiros

(57) ABSTRACT

Embodiments described herein provide methods and systems for securely communicating with electronic assets using an authenticated computer hub and a central server. The authenticated computer hub transmits a hub identity uniquely identifying the computer hub and communication results received from authenticated electronic assets, and receives an identity confirmation message and electronic asset identities to be authorized with control directives defining operational usage parameters. The authenticated computer hub has a user interface to display electronic assets granted access, and a short-range communication device to connect to authorized electronic assets to exchange information based on control directives. The methods and systems involve a central server with a non-transitory memory storing a list of authenticated hub identities, identifiers for electronic assets, control directives, and communication results from the authorized electronic assets, along with a hub manager interface, a communication interface, and a hardware processor.

20 Claims, 12 Drawing Sheets

SYSTEMS, DEVICES AND METHODS FOR SECURELY COMMUNICATING WITH ELECTRONIC ASSETS USING AN AUTHENTICATED COMPUTER HUB AND A CENTRAL SERVER

FIELD

Embodiments relate to systems and methods for secure communication between electronic assets, a computer hub, and a central server.

INTRODUCTION

Electronic assets can be used in different applications and for various support roles. Electronic assets can support short-range physical and radio frequency communication methods. The short-range electronic assets can exchange data when communication resources support short-range data exchange. Different types of electronic asserts can connect and exchange data using different types of communication methods. For example, electronic assets in the field of body health, wellness and vital signs can use Bluetooth connectivity and, in some cases, Universal Serial Bus (USB) connectivity for collecting, accessing and displaying digital readings for the purposes of personal wellness and health.

In the field of personal health and wellness, scales, blood pressure monitors, glucose monitors, oximeters and other medical appliances are being used to track different aspects of a person's health. Within the medical community, support vehicle devices (e.g. ambulances equipment), ECG monitors, ventilators, suction units, HGT blood glucose monitors can be enabled with short-range communication technology such as Bluetooth.

The use of short-range communication technologies can result in security issues. For example, a person can use electronic assets with no control over the types of electronic assets involved, their quality, permitted users of the devices, who has access to the information they produce, and so on. Getting the information from a short-range communication to a central location, like a central server, can also raise security issues. Systems can lack of control over what electronic assets are being used and the quality of each electronic asset. Some use cases or applications require secure systems. For example, medical devices with incorrect readings and inaccurate readings could be misleading and even fatal. The data may also not relate to a confirmed user.

In other situations, when collecting other electronic assets for a specific purpose, for example for use in an ambulance or an emergency medical service (EMS), there is no way to securely connect and verify the presence of these devices. There is no central method for permitting their connection into the purpose of the system. In some cases, there is a need to have an authenticated user onboard these electronic assets to ensure the quality of the overall system. Once connected there is also no central location to indicate if a device is missing when absent. In this example, such a problem leads to the possibility that emergency vehicles might drive away without all their essential equipment on board.

There exists a need for securely connecting multiple electronic assets, and using the data from the electronic assets (e.g. wellness devices, medical devices and other electronic assets). Incorporating wide-area communication technology, such as IoT (Internet of Things) communication protocols, into all electronic assets leads to both tracking issues and security vulnerabilities. Managing multiple IoT devices can be complex and expensive as each device represents a wide-area connection, with subscriber identity modules (SIM) cards, activation problems and data charges. Medical and wellness devices that support IoT network connections can be compromised using various hacking techniques. For example, a group of 19 vulnerabilities known as Ripple20 has created security issues. A complete operating system change can be result in great cost and expense. There exists a need to protect against such security vulnerabilities while minimizing device requirements or changes.

SUMMARY

Embodiments described herein relate to systems and methods for securely associating and communicating with locally connected electronic assets using an authenticated computer hub and a central server. In particular, embodiments described herein relate to systems and methods that use an authenticated computer hub and a central server to allow the identification, connection and tracking of locally connected electronic assets for the purposes of electronic asset verification, tracking and information gathering. Systems and methods further relate to authenticating the user of the authenticated computer hub to allow for the connecting of electronic assets. Systems and methods further related to the ability to track which user has accessed electronic asset data.

Embodiments described herein relate to systems and methods for verifying that all of the components that are to be connected to an authenticated computer hub are actually present (e.g. asset tracking) regardless of whether there is a specific authenticated users. For example, if an ambulance should have 10 IoT connected devices then the fact that one has gone missing within specified intervals will be noted. Embodiments described herein relate to systems and methods for alerting an individual patient who the authenticated computer hub has been allocated for. Embodiments described herein relate to systems and methods for aggregating data from multiple assets connected in a temporary setting and linking the data to a particular patient (e.g. a temporary assignment of identity to aggregated data from multiple devices).

Embodiments described herein relate to systems and methods that provides the ability to limit which electronic assets are allowed to connect and what information is collected is essential. Embodiments described herein relate to systems and methods that can track electronic assets and determine if they are missing or absent to the purpose they are intended to fulfill. Embodiments described herein relate to systems and methods that confirm the identity of the user whose information is being collected and the person or device(s) accessing and/or collecting of that information.

In accordance with an aspect, there is provided a method of securely communicating with one or more electronic assets using an authenticated computer hub and a central server. The method involves, at a central server, establishing a secure communication channel between the central server and a computer hub to receive a hub identity uniquely identifying the computer hub; creating an authenticated computer hub by matching the received hub identity against a database of authenticated computer hubs and transmitting an identity confirmation message; providing a hub manager interface to the authenticated computer hub, the computer hub manager interface for selecting and assigning one or more electronic assets and control directives defining operational usage parameters for selected and assigned electronic assets within an asset database, and securely transmitting identities of the selected and assigned electronic assets and control directives to the authenticated computer hub; receiving connection results and communication results from the authenticated computer hub when received from the selected and assigned electronic assets following the control directives provided by the hub manager interface. The method involves, at the authenticated computer hub, communicating over the secure communication channel the hub identity for verification at the central server in order to receive the identity confirmation from the central server; receiving instructions providing identifiers for the selected and assigned electronic asset that are to be granted access to the authenticated computer hub from the central server; providing a user interface indicating that the selected and assigned electronic assets have been granted access; connecting to the selected and assigned electronic assets through a short-range network and communication method providing two-way communication between the selected and assigned electronic assets and the authenticated computer hub; transmitting results of the connection attempt to the central server; executing the control directives to periodically attempt to communicate with the selected and assigned electronic assets to exchange data, and communicating over the network connection the communication results from the one or more authorized electronic assets using guidelines provided within the control directives.

In some embodiments, the short-range communication method is a Bluetooth short-range communication method.

In some embodiments, the secure communication channel uses a long-range communication method comprising an IoT long-range cellular communication method.

In some embodiments, the communication results comprise failure to communicate with one or more of the selected and assigned electronic assets.

In some embodiments, the method involves verifying a user operating the user interface in order to couple with one or more authorized electronic assets through a biometric authentication process.

In some embodiments, the method involves, at the authenticated computer hub, continuously monitoring the status of the connection to the one or more electronic assets.

In some embodiments, the method involves, prior to providing the user interface, receiving a biometric confirmation for the authenticated computer hub.

In some embodiments, the method involves using the biometric confirmation to identify who collected data from an electronic asset associated with the authenticated computer hub after receiving the biometric confirmation.

In some embodiments, the method involves associating an electronic asset to another physical object to generate an authorized electronic asset.

In some embodiments, the method involves displaying, using the control directives, visualizations of data corresponding to readings received from one or more assets.

In some embodiments, the method involves, at the authenticated computer hub, receiving a message from a first electronic asset and sending a control message to a second electronic asset based on a value extracted from the first message.

In some embodiments, the communication results from a computer hub and one or more authorized electronic assets is used to build statistic analysis charts;

In some embodiments, the method involves anonymizing the communication results from the authenticated computer hub and one or more authorized electronic assets using with an artificial intelligence process to produce statistically useful patterns within the data set.

In another aspect, embodiments described herein provide a system for securely communicating with one or more electronic assets to using an authenticated computer hub and a central server. The system has an authenticated computer hub having: a communication device for transmitting a hub identity uniquely identifying the computer hub and communication results received from one or more authenticated electronic assets to a central server, and for receiving an identity confirmation message and electronic asset identities to be authorized with control directives defining operational usage parameters; a user interface to display that one or more electronic assets have been granted access and to connect to one or more authorized electronic assets; a short-range communication device to enable a user to connect to one or more electronic assets and to communicate with the one or more authorized electronic assets to exchange information based on control directives. The system has a central server having: a non-transitory memory storing a list of authenticated hub identities, one or more identifiers for electronic assets, control directives, and a received communication results from the one or more authorized electronic assets; a hub manager interface for selecting the authenticated computer hub and defining electronic assets and control directives for connecting to the authenticated computer hub; a communication interface for: receiving hub identity requests, connection results from attempts to connect authorized electronic assets and communication results from attempts to communicate with authorized electronic assets; transmitting a hub identity confirmation message, one or more authorized electronic asset identities and control directives defining operational usage parameters of those devices; a hardware processor for: computing matching results of received hub identities against known hub identities to create authorized hub identities; determining additional actions based on connection results from connection attempts made with one or more authorized electronic assets and communication results from attempts to communicate with the one or more electronic assets, and building communication charts based on information received from the one or more devices via the authorized computer showing the time each communication attempt was performed and the results.

In some embodiments, the authenticated computer hub is a medical device that generates patient medical data while supporting the authorizing electronic assets.

In some embodiments, the authenticated computer hub is dedicated to watching the status of the connection to one or more electronic assets.

In some embodiments, the user interface requires a biometric confirmation before the computer hub can be used.

In some embodiments, the biometric confirmation is used to identify who collected data from an electronic asset associated with the computer hub after biometric confirmation.

In some embodiments, the electronic asset is associated to another physical object enabling it to become an authorized electronic asset.

In some embodiments, the control directives can display a chart of information corresponding to readings received from one or more assets.

In some embodiments, the computer hub can receive a message from one electronic asset and send a control message to a second electronic asset based on the value found within the first message.

In some embodiments, the short-range communication method is a Bluetooth short-range communication method.

In some embodiments, the long-range communication method is an IoT long-range cellular communication method.

In some embodiments, the communication results can include the failure to communicate with one or more of the authorized electronic assets.

In some embodiments, the authenticated computer hub is dedicated to watching the status of the connection to one or more electronic assets.

In some embodiments, the communication results from a computer hub and one or more authorized electronic assets is used to build statistic analysis charts.

In some embodiments, the communication results from a computer hub and one or more authorized electronic assets is anonymized and used with an artificial intelligence process to produce statistically useful patterns within the data set.

In another aspect, there is provided a system for securely communicating with one or more electronic assets. The system has an authenticated computer hub and a central server. The authenticated computer hub has a communication device for transmitting a hub identity uniquely identifying the computer hub and communication results received from one or more authenticated electronic assets to a central server, and for receiving an identity confirmation message and electronic asset identities to be authorized with control directives defining operational usage parameters. The authenticated computer hub a user interface to display that one or more electronic assets have been granted access and to connect to one or more authorized electronic assets. The authenticated computer hub has a short-range communication device to enable a user to connect to one or more electronic assets and to communicate with the one or more authorized electronic assets to exchange information based on control directives.

The central server has a non-transitory memory storing a list of authenticated hub identities, one or more identifiers for electronic assets, control directives, and a received communication results from the one or more authorized electronic assets. The central server has a hub manager interface for selecting the authenticated computer hub and defining electronic assets and control directives for connecting to the authenticated computer hub. The central server has a communication interface for: receiving hub identity requests, connection results from attempts to connect authorized electronic assets and communication results from attempts to communicate with authorized electronic assets; and transmitting a hub identity confirmation message, one or more authorized electronic asset identities and control directives defining operational usage parameters of those devices.

The central server has a hardware processor for: computing authorized hub identities; computing additional actions based on connection results from connection attempts made with one or more authorized electronic assets and communication results from attempts to communicate with the one or more electronic assets, and transmitting output data computed based on information received from the one or more devices via the authorized computer indicating communication results.

In another aspect, there is provided an authenticated computer hub for securely communicating with one or more electronic assets. The authenticated computer hub has a communication device for transmitting a hub identity uniquely identifying the computer hub and communication results received from one or more authenticated electronic assets to a central server, and for receiving an identity confirmation message and electronic asset identities to be authorized with control directives defining operational usage parameters. The authenticated computer hub a user interface to display that one or more electronic assets have been granted access and to connect to one or more authorized electronic assets. The authenticated computer hub has a short-range communication device to enable a user to connect to one or more electronic assets and to communicate with the one or more authorized electronic assets to exchange information based on control directives.

In another aspect, there is provided a central server for securely communicating with one or more electronic assets. The central server has a non-transitory memory storing a list of authenticated hub identities, one or more identifiers for electronic assets, control directives, and a received communication results from the one or more authorized electronic assets. The central server has a hub manager interface for selecting the authenticated computer hub and defining electronic assets and control directives for connecting to the authenticated computer hub. The central server has a communication interface for: receiving hub identity requests, connection results from attempts to connect authorized electronic assets and communication results from attempts to communicate with authorized electronic assets; and transmitting a hub identity confirmation message, one or more authorized electronic asset identities and control directives defining operational usage parameters of those devices. The central server has a hardware processor for: computing authorized hub identities; computing additional actions based on connection results from connection attempts made with one or more authorized electronic assets and communication results from attempts to communicate with the one or more electronic assets, and transmitting output data computed based on information received from the one or more devices via the authorized computer indicating communication results.

Other aspects of various embodiments are described herein.

BRIEF DESCRIPTION OF DRAWINGS

The following detailed description can be read in conjunction with the included figures. The included figures are intended to illustrate at least one example implementation. These exemplary illustrations are not intended to limit the disclosure to the specific embodiments shown herein.

DETAILED DESCRIPTION

Figure 1:
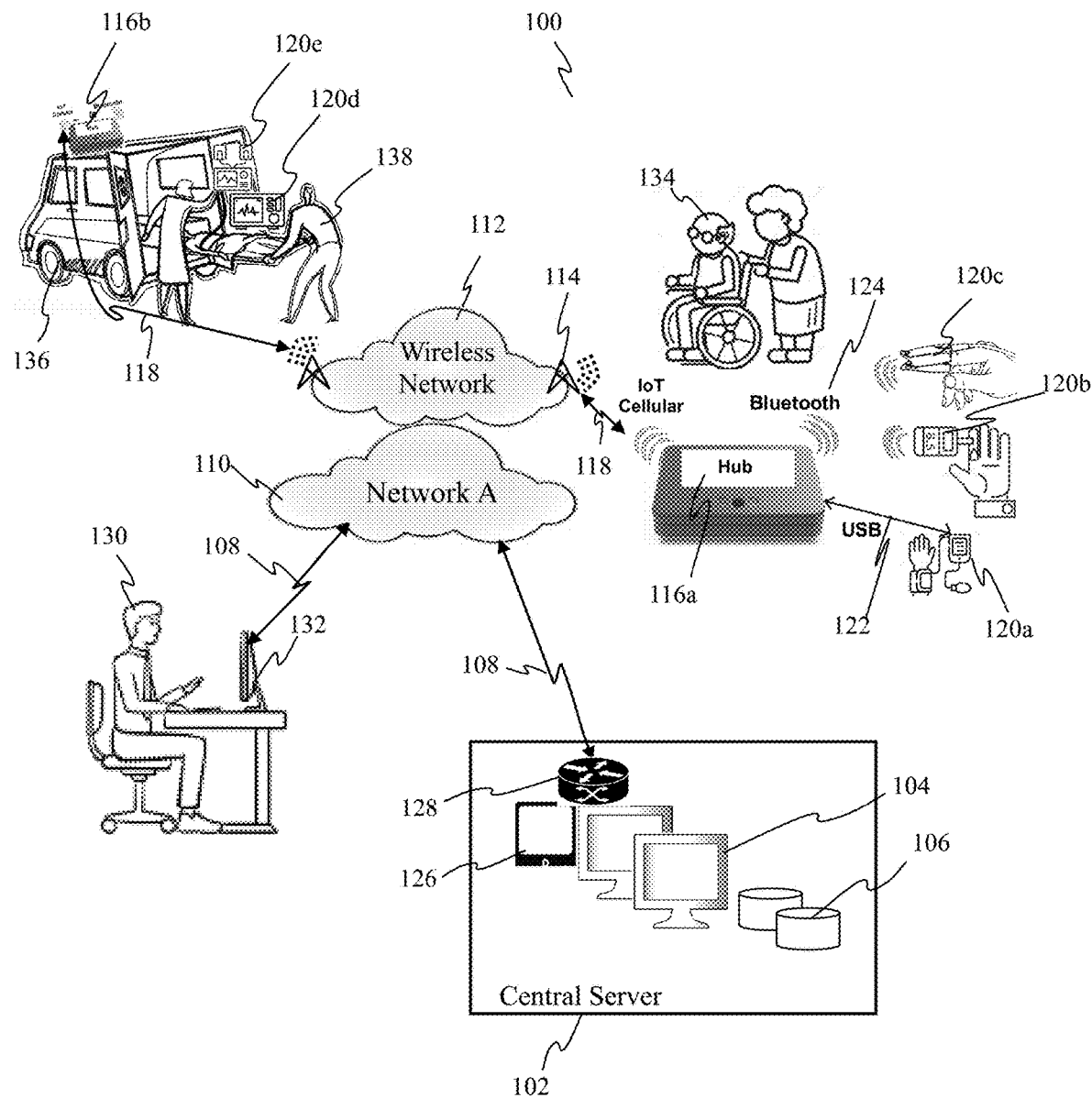
FIG. 1 shows an illustration of a network overview with a central server communicating through a computer hub with one or more electronic assets.

Embodiments described herein provide a method of securely communicating with one or more electronic assets using an authenticated computer hub and a central server. The method involves a central server establishing a wide-area secure communication channel with a computer hub to receive a computer hub identity unique to the computer hub, 'hub identity'.

Electronic assets can be computer systems (e.g. hardware processor and non-transitory memory storing instructions) that are capable of supporting two way communications to a computer hub using a short-range communication method. In some embodiments, the electronic asset is specifically selected for its manufacturing origins, and communication and tracking is performed directly with the electronic asset. In other embodiments, the electronic asset is associated with an item. This electronic asset can be considered a proxy-agent for another physical item, and as a proxy-agent the electronic asset can report on the location and general state of operation of the physical item it is proxying.

The method involves the central server matching the received hub identity against a database of known computer hubs to create an authenticated computer hub, and transmitting an identity confirmation message upon completing the match. The central server stores hub identities for known computer hubs in the database.

The central server provides a hub manager interface for selecting and assigning one or more authorized electronic assets and control directives defining operational usage parameters for the assigned electronic assets within an asset database to an authenticated computer hub. The central server securely transmits the identities of the assigned electronic assets and control directives to the authenticated computer hub.

The central server further receives connection results and communication results from the authenticated computer hub when received from the one or more authenticated electronic assets following control directives provided by a hub manager. The central server can store the received results.

The authenticated computer hub communicates, over a wide-area network, a hub identity for verification at a hub identity database within a central server in order to receive an identity confirmation. The hub identity database stores the hub identities to provide a repository for authenticating computer hubs.

The authenticated computer hub receives instructions providing electronic asset identities that are to be granted access to the authenticated computer hub from the central server.

The authenticated computer hub provides a user interface indicating or displaying one or more electronic assets have been granted access and to connect the one or more electronic assets through a short-range network in order to provide two-way communication. For example, the user interface can be displayed to a user to inform the user of the one or more electronic assets have been granted access.

The authenticated computer hub uses a short-range communication method to allow the user to connect one or more authorized electronic assets to the authenticated computer hub and transmits the result of the connection attempt to the central server.

The authenticated computer hub executes the control directives (and follows the guidelines within) to periodically attempt to communicate with the one or more authorized electronic assets to exchange information. The authenticated computer hub subsequently communicates over a wide-area network the connection and communication results from the one or more authorized electronic assets following the guidelines provided within the control directives.

FIG. 1 shows an illustration of a system 100 with a central server 102 communicating 108 through a computer hub 116 to one or more electronic assets 120.

The system 100 is for securely communicating with one or more electronic assets 120 using an authenticated computer hub 116 and a central server 102. The authenticated computer hub 116 has a communication device for transmitting a hub identity uniquely identifying the computer hub and communication results received from one or more authenticated electronic assets to a central server, and for receiving an identity confirmation message and electronic asset identities to be authorized with control directives defining operational usage parameters. The authenticated computer hub 116 has a user interface to display that electronic assets 120 have been granted access and to connect to authorized electronic assets 120. The authenticated computer hub 116 has a short-range communication device to enable a user to connect to the electronic assets 120 and to communicate with the authorized electronic assets 120 to exchange information based on control directives.

The system 100 has a central server 102 with a non-transitory memory storing a list of authenticated hub identities, one or more identifiers for electronic assets, control directives, and received communication results from the one or more authorized electronic assets. The central server 102 has a hub manager interface for selecting the authenticated computer hub 116 and defining electronic assets 120 and control directives for connecting to the authenticated computer hub 116. The central server 102 has a communication interface for receiving hub identity requests, connection results from attempts to connect authorized electronic assets 120 and communication results from attempts to communicate with authorized electronic assets 120. The central server 102 also transmits a hub identity confirmation message, one or more authorized electronic asset identities and control directives defining operational usage parameters of those devices. The central server 102 has a hardware processor for computing matching results of received hub identities against known hub identities to create authorized hub identities, determining additional actions based on connection results from connection attempts made with authorized electronic assets 120 and communication results from attempts to communicate with the electronic assets 120. The central server 102 also builds communication charts based on information received from the one or more devices via the authorized computer showing the time each communication attempt was performed and the results.

Further details of the components of system 100 are provided herein.

The Central Server

In some embodiments, the central server 102 can be a cluster of computers resources 104 with various functions. There are database resources 106, user interface (UI) resources 126, load balancing resources, communication routing and communication interface resources 128, and so on. There are also firewall resources 128, local area networking resources and additional computer systems 104 for dealing with rising computational requirements.

In some embodiments, the central server 102 is operating in a cloud computing environment that is hosted by another company specializing in selling computer processing resources. In other embodiments the central server 102 is running on computer resources physically located within an organization like, a public facility like a hospital, long-term care home, development company, trucking company or other environments where the system can be utilized. The central server 102 is a dedicated software program utilizing CPU resources for complex operations around identification, control, management and tracking of computer hub devices 116 ("computer hubs").

The central server 102 is often utilized with electronic assets 120 that are moveable and transportable, thus allowing embodiments with moving assets 120, temporarily assigned assets 120 and assets 120 that are valuable and must be tracked. The central server 102 and computer hub 116 work together to provide a cost effective and efficient way to track electronic assets 120 without forcing every single asset to become an Internet of Things (IoT) carrier with its own subscriber identity module (SIM) card, setup fees and cost issues.

Communication 108 from the central server 102 to other computer systems (e.g. computer hubs 116, laptops, desktop computers, mobile devices, cell phone computers 132) is facilitated through one or more computer networks 110, 112. These networks 110, 112 can be public or private, such as virtual private network (VPNs) or the Internet. The network 110 can utilize physical connections 108, such as fibre optic links, dedicated phone lines and other physical links, to facilitate communication messages. The network 112 might also support wide-area wireless network 112 connections and support base station 114 and cellular links that have a range of miles and use a wide variety of radio frequency (RF) methods. For example, these can be 3G, 4G and 5G networks based on GSM, GPRS, Edge, UMTS and other protocols. These wireless networks 112 can also support Internet of Things (IoT) protocols like LTE-M (Machine Type Communication), including LTE Cat-M1 (LTE-M1) and other protocols. Interconnectivity between one or more networks 110, 112 is known through network address translators (NATs), advanced routing hubs and protocol methods.

The Computer Hub

The computer hub 116 to be managed is a computer device containing a CPU, different types of data communication capabilities, in some embodiments interfaces (e.g. audible and visual user interfaces) and in some embodiments input devices like buttons, knobs and touchscreens. The computer hub 116 is built with (or assigned) a unique computer hub identity ("hub identity"). This hub identity can be established or stored within the central server 102 using several different embodiments to be described herein. The hub identity is private and is held within protected and database 106 in non-transitory memory, within the central server 102 or securely coupled thereto.

The computer hub 116 can be of different physical sizes, such as small like a watch-type device or wearable device, a cell phone, PDA, laptop, or large such as a desktop computer. In some embodiments the computer hub 116 might serve several uses. The computer hub 116 might also dispense drugs or medications for a patient 134, for example. The computer hub 116 might also be a person's cell phone 116 with a processor running a computer hub 116 application (stored in memory) that has been built to communication with the central server 102 for the purposes of connecting, tracking and management electronic assets 120.

The computer hub 116 can have different additional capabilities depending on the environment it is used in. In some embodiments, the computer hub 116 might have global positioning satellite (GPS) support, accelerometers, altimeters, LCD screens, biometric input sensors, lights, buttons, wearable patches, thermoreceptors, mechanoreceptors, nociceptors, photoreceptors, and chemoreceptors and other input/output capabilities. For example, in some embodiments, a message can be sent from a sensor within an ingested pill to a wearable patch. The patch transmits the information to a computer hub 116 running as a mobile application so that patients can track the ingestion of the medication on their smart phone and at the central server 102. Patients can also permit their caregivers and physician to access the information through a web-based portal on the central server 102. In addition, the computer hub 116 could also be fire or water resistant, or tamper-detecting or tamper-proof and ruggedized. It might be mounted in a vehicle or on a vehicle to improve coverage conditions. In some embodiments it might have external antennas to improve radio frequency (RF) communication range.

The computer hub 116 is capable of supporting multiple types of data communication methods. These methods can include wide-area cellular radio frequency (RF) protocols, mid-range Wi-Fi (802.11) RF protocols, shorter-range Bluetooth™ protocols 124, near field communications (NFC) and physical connections such as a universal serial bus (USB) 122, for example. In some embodiments point-to-point (P2P) radio technology can be used to connect shorter-range devices (e.g. IoT devices) to the computer hub 116 to further relay information to the central server 102.

For connecting to and communicating with one or more locally connected electronic assets 120 ("electronic assets"), the computer hub 116 is capable of terminating communications links 122, 124. Termination is a method of supporting the link as a final destination for message exchange. The communication is not routed to another endpoint like a wide-area network 110, 112 that is capable of sending these messages to the central server 102. A terminating endpoint the computer hub 116 can also protect one or more electronic assets 120 from incoming communications from outside sources. This endpoint behaviour can provide a solution to external hacking, intrusion and theft of information from nefarious hackers and illegal behaviour.

This local termination capability can be referred to as 'short-range communication' herein. Although in some embodiments using a Wi-Fi communication method would not be considered short-range, using "Wi-Fi direct", which is a method of direct point-to-point communication for providing an electronic asset 120 an instant termination point at the computer hub 116.

In other embodiments, the local electronic assets 120 are connected using different methods supported by the computer hub 116. These could include Wi-Fi direct, Bluetooth, NFC various proprietary protocols, universal serial bus (USB) and others. In other embodiments low-powered IoT capabilities allow for a point-to-point IoT local area network communication with the computer hub 116.

The computer hub 116 can communicate to computer networks 110, 112 capable of reaching the central server 102. In some embodiments the computer hub 116 is able to take advantage of cellular links 118 using IoT cellular protocols like LTE-M1 and others. With embedded IoT chipsets, these computer hubs 116 have the power and range to reach very distant base stations 114 on wide-area wireless networks 112. Computer hub 116 communications 108 that takes advantage of one or more networks to reach the central server 102 are termed 'wide-area communications' herein.

In other embodiments the computer hub 116 can take advantage of Wi-Fi network protocols and connections to reach the central server 102. Such configurations might be more popular in a closed environment, such as within an organization or a hospital setting or long-term care home settings. The computer hub 116 acts as a consolidation point to help manage, protect and communicate to locally connected electronic assets, on behalf of the central server 102. The computer hub 116 can act as a proxy executing instructions on behalf of the central server 102.

The central server 102 can control the computer hub 116. For example, the central server 102 can control the computer hub 116 so that it cannot add or remove electronic assets 120 autonomously. This can ensure electronic assets are of a certain quality, they are known, they are trackable, and they cannot be easily stolen without the computer hub 116 being aware of the theft.

The decisions to connect and terminate communication links with electronic assets is guided through a UI 126 provided at the central server 102. A user 134, 138 at the computer hub 116 might control the timing of the connection, but not whether it is permissible or not. An electronic asset manager 130 guides the oversite in the system which will be examined in later paragraphs.

The Electronic Asset

As mentioned, these computer hubs 116 can support short-range communication methods 122, 124 to communicate to electronic assets 120. These electronic assets 120 can perform a wide range of services depending on the environment they are placed in. In the medical community these electronic assets 120 could be for personal use for a patient 134 like blood pressure 120a monitors, blood glucose monitoring 120b or blood oxygen monitoring 120c, and so on. In a mobile environment 136, they could include electronic assets 120 for heart defibrillation 120e, intravenous blood infusion, anesthesia monitors, body temperature monitoring, electrocardiography machines (ECG) 120d and other types of electronic assets 120.

In other fields, e.g. firefighting, electronic assets 120 could also include electronic water pressure monitors, electronic CO2 monitors, electronic fire extinguishers, electronic ventilator fans, short-wave radios, electronic thermal imaging cameras and other electronic assets 120.

Other example fields include home security, delivery services, drone operations, vertical take-off and landing (VTOL) equipment, auto-drive taxi services and many other fields of endeavour now and those in the future. The contents of a mobile vehicle like EMS trucks 136, ambulance 136, VTOL and taxis may all carry a range of electronic assets that need tracking. There are also embodiments in the home and business environment where electronic assets might require categorization, monitoring and tracking.

In other embodiments, the electronic asset 120 is associated to another physical object and together they may be referred to as an authorized electronic asset 120. In some embodiments the electronic asset 120 is a self-contained computer system that is affixed to the physical object to be tracked. For example, an electronic asset tag 120 can be screwed into or welded onto heavy machinery at a construction site to ensure that nothing on the construction site is stolen or removed from the site without authorization. The computer hub manager 130 can assign one or more computer hubs 116 to the construction site (e.g. depending on the area of the site) to track the assigned computer assets 120 for the required job. The electronic asset tag 120 might use communication methods like Bluetooth, near-field communication (short-range RFID), long-range RFID or a proprietary communication method to communicate with the computer hub 116.

In other embodiments, an electronic asset 120 that is associated with another physical object performs a coupling to that object to detect whether it is powered on, running and performing activities. There could also be GPS within the electronic asset 120 to track movement and speed. The coupling could be physical, like a USB connection or it could be wireless like NFC, Industrial IoT (IIoT) or many kinds of proprietary links.

Authentication of Computer Hubs

The computer hub 116 has a unique hub identity. In some embodiments the hub identity is injected into or contained within the computer hub 116, such as an encryption certificate, for example. Encryption certificates can be used for encrypting data and verifying communication entities. In one embodiment a certification could be created by a certificate authority (CA). In another embodiment, the central server 102 acting as the CA creates a certificate. In these embodiments the unique certification can be exchanged in a secure location, such as a manufacturing plant, as each computer hub is first powered up and tested at the completion of manufacturing.

In another embodiment, the computer hub 116 generates a unique public and private encryption key pair and provides that directly to the central server 102 during manufacturing. Alternatively, the public of the central server 102 is provided to the computer hub 116 during manufacturing and it encrypts its own unique hub identity during data exchange (e.g. as part of an initial data exchange, or all data exchanges) with the central server 102.

In some embodiments, a unique serial number is extracted from the CPU chip used within the computer hub 116. For example, a chip manufacture can provide a device identifier in the CPU chips. If there is a hardware network interface device used in the computer hub then a media access control address (MAC address) that is unique can be used as an identity. As another example, Electronic Product Code (EPC) can be built into the PCB and then exchanged with the central server 102 as the hub identity.

To protect the hub identity on the computer hub 116 different security measures can be used. In one embodiment, a secure enclave method is employed that allows data to be written into the security enclave, but it can never be accessed again after that. Any use of the calculation or operations performed with the information would take place by software running only within the secure enclave. For example, a private encryption key could be placed into the secure enclave and encryption could be performed within the secure enclave on the hub identity before being transmitted to the central server 102. The public key can be used to decrypt the hub identity for matching against the stored hub identity in the central server 102.

This hub identity is then exchanged between the computer hub 116 and the central server 102 and is saved in non-transitory database memory 106 for both endpoints. Since both endpoints have this shared hub identity, it can be used for creating a secure and unbreakable connection for hub control messages, hub connection messages and hub data messages that are sent and received by the computer hub 116.

When the computer hub 116 is first activated, or when a computer hub 116 app is turned on, the computer hub 116 communicates with the central server 102 for authentication. When authentication is granted then can messages be exchanged and electronic assets 120 be added, removed, managed and tracked.

The Computer Hub Manager

The central server 102 is directed into action by a computer hub manager 130. Using an access method like a desktop computer 132, laptop computer, personal digital assistant, tablet computer or mobile device like a cell phone the computer hub manager 130 can access the UI 126 at the central server 102.

The computer hub manager 130 has gained authorization to the central server 102 through many possible embodiments. In medical embodiments the computer hub manager 130 could be a doctor, nurse, pharmacist, long-term care worker, a personal support worker (PSW) or some other healthcare worker. In transportation embodiments the computer hub manager 130 could be a company employee, a flight attendant, taxi attendant, manager of a company or some other senior employee. The computer hub manager 130 can determine what electronic assets 120 to associate with one or more computer hubs 116 for monitoring and communication.

In some embodiments, one or more specialized workers within a company might be given authorization as computer hub managers 130. For example, a company offering EMS and ambulance services might be running a central server 102 within their company and manage electronic assets 120 across their fleet of EMS vehicles.

In other embodiments a governing body (e.g. the College of Physicians and Surgeons) can have an authorization database of all members (e.g. doctors, nurses, surgeons) that want to act as computer hub managers 130. These individuals might want to gain access to computer hubs 116 to assign electronic assets 120 to patients on a 'as needed' basis.

Examples of the Process Flow

In one medical embodiment, a doctor 130 decides that their patient 134 requires special attention due to a recent surgery and discharge from the hospital. The doctor or their assistant 130 then log into the central server 130 through the UI 126 and indicate the make, model and in some embodiments the serial number of the medical vital sign electronic assets 120a, 120b, 120c they intend for that patient 134. In this example they prescribe a medical grade USB capable, blood pressure monitor 120a, a Bluetooth capable glucose monitor 120b and a Bluetooth oximeter 120c for the patient 134 to use several times per day.

The patient might already have their computer hub 116a at home and it might be already serving a purpose, for example it could be acting as a pill dispenser 116a for the patient 134. In another embodiments, when the patient leaves the hospital, they might be provided the computer hub 116a as they depart including one or more vital sign monitors 120a, 120b, 120c. In some embodiments the computer hub 116 might be registered to the patient 134 or even biometrically accessible only by the patient.

When the patient 134 arrives home they would then proceed to turn on their computer hub 116a and activate the various vital signs electronic assets they have been provided 120a, 120b, 120c.

When turned on, the computer hub 116a first communicates with the central server 102 for authentication. Only after it attains the authenticated stage can it being to send and receive messages about electronic assets 120. The computer hub 116a will then receive electronic asset 120 assignment and control directives established by the computer hub manager 130 related to this computer hub 116a once it is authenticated.

Only after the computer hub 116a receives control directives related to connecting electronic assets 120 it will begin to notify the patient that changes have taken place. Depending on the embodiment and the capabilities of the computer hub 116a different methods could be used to inform the user 134 that the computer hub 116a has been authorized to accept the connection of electronic assets 120a, 120b, 120c.

In some embodiments when the computer hub 116a has an LCD display a visual message could be updated to indicate that one or more electronic assets 120 can now be connected through the computer hub 116a. In another embodiment the computer hub 116a might make an audible noise, it might flash a blue light to indicate that Bluetooth pairing is now possible.

In other embodiments the computer hub 116 might require that only a registered person be allowed to initiate a connection to an electronic asset 120. For example, a patient 134 might have registered their biometric with the computer hub 116a so it can be used for other purposes like dispensing their daily medications. Only when this same patient 134 re-enters their biometric identification will the computer hub 116a authorize the connection to the identified electronic asset 120. This level of security ensures that other random individuals are not able to alter the setup of the computer hub 116 which further helps to protect all operation.

In another embodiment authorization is given to a person to initiate changes to the computer hub 116 through a near field RFID communication. This is also termed near-field communication (NFC) and it uses an induction coil to energize a passive CPU within an NFC enabled lanyard or identification badge. A computer hub 116 manager might first tap their badge to enable electronic assets 120 to connect. Additionally, an NFC communication could be used to authorize specialized computer hub 116 actions, for example dispensing medications. A patient might use the NFC communication or a long-term care home employee, a loved one or some other caregiver like a personal support worker (PSW).

When the patient 134 has acknowledged the message and turned on the electronic asset 120 can connection be initiated. The original control directive from the central server 102 also includes various types of identification parameters for the electronic asset 120. This can vary with different embodiments. In one embodiment the computer hub manager 130 was able to select the electronic asset 120 by asset type, asset model and even asset serial number. In other embodiments only the electronic asset type might be provided. This identification is important to ensure that only the correct electronic asset 120a, 120b, 120c is connected and that it matches the quality and specification expected by the computer hub manager 130.

Once connected the patient 134 can start to take advantage of these electronic assets 120 for the purposes they are intended. This might involve collection of vital statistics like blood pressure, weight, oxygen levels, glucose levels and many other patient vitals. In some embodiments the computer hub manager 130 has also recommended specific times to use the electronic assets 120. Depending on the capabilities of the computer hub it might display a reminder to the patient 134, it could beep, flash a light or use other methods to ensure personal vitals are collected in a timely fashion.

In some embodiments the computer hub manager 130 has specialized knowledge about the electronic assets 120. For example, an endocrinologist working with a patient 134 with severe type 2 diabetes is likely to understand the specific readings provided by an electronic asset that monitors glucose levels in a patient. Using this knowledge, the endocrinologist 130 can specify control directives to the computer hub 116 with actions relative to the readings that are returned from the computer hub 116 accepting the readings from the glucose monitor 120. Using this knowledge, the endocrinologist 130 can then specify additional control directives to direct the operation of a Bluetooth insulin pen for injection within specified dosing ranges based on their real-time glucose readings.

In another embodiment the computer hub manager 130 is a community pharmacist 130 that manages several patients using suboxone to deal with some patients that need pharmacist witnessing of medication consumption. In other examples, sometimes patients with severe mental health challenges are opposed to taking their medications, leading to dangerous and unpredictable behaviours. Using the computer hub 116 as a medication dispenser 116*a* they are able to connect a specialized Bluetooth RFID reader that reads a message off a medication consumption tag worn by the medication consumer 134. This tag picks up a signal when medication injected by the medication consumer 134 are broken down by stomach acids. When the signal is received and given to the medication dispenser 116*a* it has received control directives that indicate it is allowed to release the next dose when that dosing period is reached. In this way the medication consumer 134 is not able to take excessive amount of medications without confirmation, while at the same time the consumption of the medications can be confirmed by the system.

In another embodiment, there are mobile environments 136 that have unique electronic assets 120. In this example paramedics 138 are using their ambulance to pickup and care for a sick patient. Their vehicle 136 could be full of equipment and many electronic assets 120*d*, 120*e*. In this example, the ECG electronic asset 120*d* and the defibrillator electronic asset 120*e* are highlighted. The computer hub 116*b* resides on the top of the vehicle 136 to assist RF coverage and to provide an external antenna.

Before the initial use of this ambulance 138 and before this accident occurred, a computer hub manager 130 worked with one or more paramedics 138 to outfit the ambulance 138 with all the necessary electronic assets 120*d*, 120*e*. The electronic assets 120 chosen were carefully selected to ensure the paramedics would be efficient, effective, and able to handle any emergency. In many cases these are portable devices, especially important in the case of roadside accidents. Connecting into the central server 102 directly from a wide range of small electronic assets 120 is not practical or realistic.

Additionally, the computer hub manager 130 wants to ensure these electronic assets 120 are not stolen or lost during the course of the day. So the computer hub manager 130 takes the time to assign specific computer assets 120 to a specific vehicle. The vehicle could be an ambulance, a VTOL, a self-driving taxi or any vehicle with important and in some cases expensive electronic assets. For example, if a public VTOL was being used to transport customers within a city or between cities, it would be important to have a defibrillator onboard in case of emergencies during the flight.

So depending on the embodiment, the computer hub manager 130 is able to select one or more of the make, model and serial number of each electronic asset 120 and assign it to the computer hub 116*b*. The paramedic 138 using the computer hub 116*b* interface then can accept and connect each electronic asset 120 as assigned to their vehicle.

Another advantage of the computer hub 116*b* would be its ability use its GPS capabilities to detect movement. If movement is detected then it can quickly review all assigned electronic assets 120*d*, 120*e* to confirm they are all connected and accounted for. Movement of the computer hub 116*b* is important as there are many situations where the electronic asset 120 might move out of range or loose connection temporarily with the computer hub 120 but it is not considered stolen or lost immediately and excessive warning, beeping and alerting could be counter-productive.

The computer hub 116*b* is also capable of accepting a biometric or NFC input from the ambulance attendant 138 with a name or identification number of the person they are about to take vitals for. This additional level of data collection can then be relayed onto the central server 102 along with all the data received from one or more electronic assets 120. The correlation of data and injured person would be very helpful to medical personnel waiting at the ER for the person involved in the accident to arrive.

For example, at the scene of an accident the paramedic 138 does not want to forget their ECG machine 120*d* on the ground buried in the snow or pushed over in the grass before they drive away. Depending the on the capabilities of the computer hub 116*b* it might be capable of beeping, displaying a message or warning the paramedic 138 that an electronic asset 120 is not accounted for.

Another advantage of the computer hub 116*b* is that information collected on the scene of the accident by electronic assets 120*d*, 120*e* can be quickly related to the central server 102 and presented to one or more professionals. Even if the electronic asset 120*d*, 120*e* is temporarily out of range it could collect the information and when back into range upload it immediately to the computer hub 116*b*. The experts viewing this information through the central server 102 can also be confident that the best equipment is being used, approved and certified by the computer hub manager 130.

Figure 2:
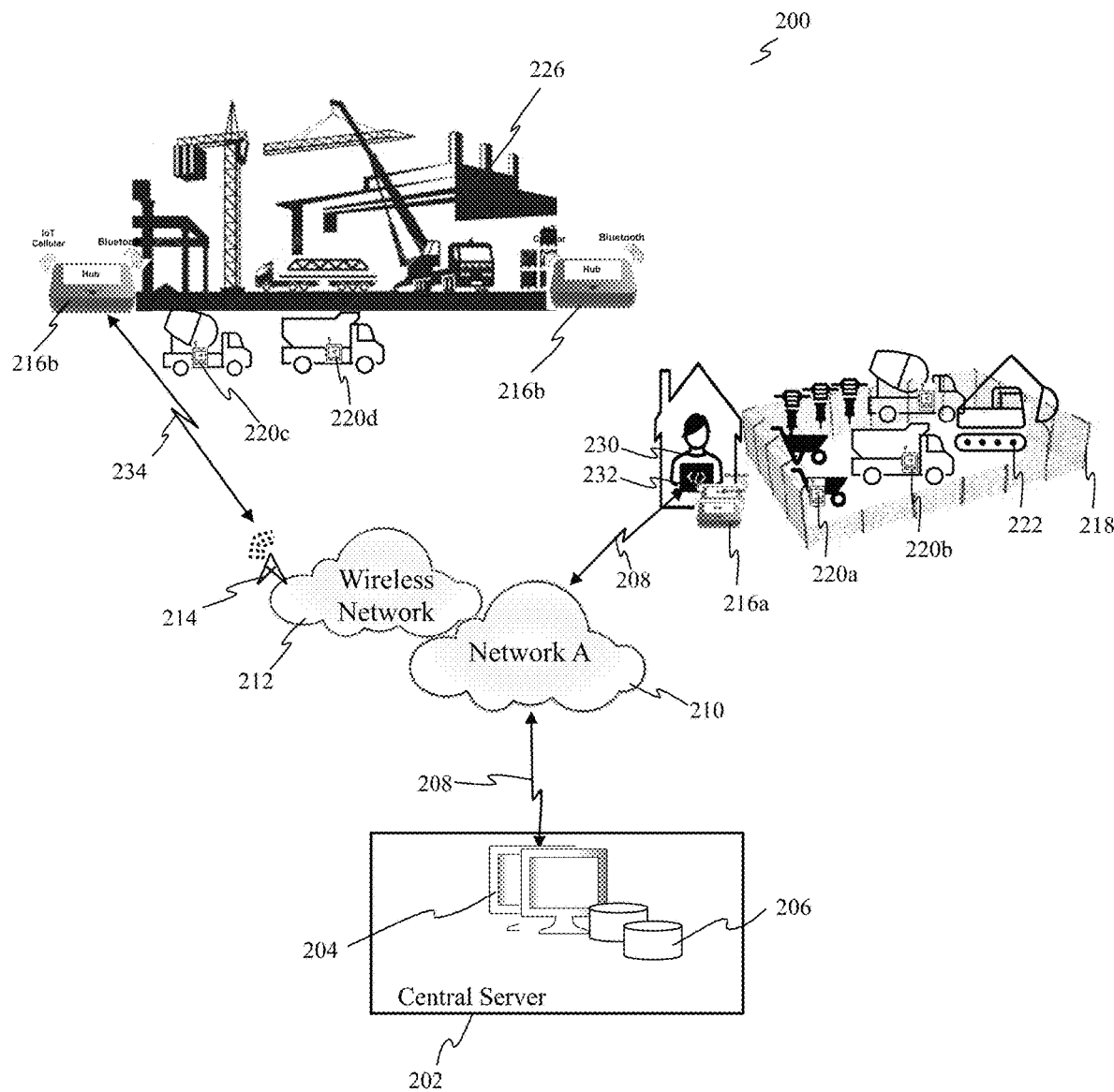
FIG. 2 shows a second embodiment of a network overview with a central server communicating through a computer hub with one or more electronic assets.

Moving to another embodiment FIG. 2 shows network overview 200 with a central server 202 communicating through a computer hub 216 to one or more electronic assets 220. As shown in FIG. 1, the central server 202 is composed of many resources like database resources 206, user interface resources 204, communication resources 208, routing resources, load balancing resources and firewall protect resources to name just a few.

The central server 202 communicates through one or more networks 210, 212 to reach the computer hub 216 wherever it might be deployed. As discussed these networks 210, 212 are terrestrial, they could be satellite based networks, Wi-Fi networks, IoT networks both wired and wireless. Routing services between these networks use network address translators (NATs) and other addressing methods to route quick and efficiently through each network to reach their intended recipient.

As described in FIG. 1 the system uses an authenticated relationship between a central server 202 and a computer hub 216 identity. This 'hub identity' is first verified with the central server 202 using communication links 208 through one or more shared wide-area networks 210, 212. These preamble steps were well explained in FIG. 1 and result in an authenticated computer hub 216 capable of having electronic assets 220 assigned to it.

Unlike other systems, a computer hub manager 230 must use a computer 232 to connect into the central server 202 login and be authorized to work with computer hubs 216 and assign electronic assets 220 to them. This authorization might come through a specific company that has registered for the service, it could be a central server 202 running within an organization, like a hospital or long-term care home or an official accredited body like the college of physicians and surgeons have provided the authority to grant access to the authenticated computer hubs 216.

In this embodiment the electronic assets 220 are stand-alone units, all identical, self-powered and autonomous. They can be associated with another physical item 222. In some embodiments these other physical items 222 are of higher value, are moveable and the need to keep tabs on them can save money to detect and avoid theft from taking place. Instead of placing a full IoT tracking system on each physical object at great expense and bother, this system using a low-cost localized method of tracking these unique objects. In some embodiments the association of the electronic asset 220 to the physical item 222 is done by attaching with screws, bolts or even welding processes. Keeping the electronic asset 220 connected with the other physical item 222 is essential for the computer hub's 216 ability to keep tabs on the physical item 222 of concern.

In this example, the computer hub manager 230 is working with their computer 232 at the central office and storage yard of the physical items 222 to be tracked and accounted for. This example involved construction equipment like dump and cement trucks, wheelbarrows, jack hammers and steam shovels 222. In other embodiments these other objects could be major farming operation or a large cannabis growing operation with advanced machinery. The system can be used where expensive, moveable items need to be tracked in a relatively small and confided area.

The computer hub manager 230 has the option of selecting one or more computer hubs 216a and the electronic assets 220a, 220b they wish to use at the storage yard 218. In this embodiment, the computer hub manager 230 has all the potential other items 222 at the storage yard 218 before they even leave to the jobs site 226. They log into the central server 202 where a database allows them to associate the electronic asset 220a, 220b to a specific item in the storage yard 218. The total number of items has already been setup by the construction company running the operation. Even if the computer hub manager 230 has performed some number of assignments at the storage yard 218, they can also perform additional assignments at the job site 226 if additional items are required to finished the job.

In another embodiment, the computer hub manager 230 could also assign computer hubs 216b at the job site 226 and wait until the other items of interest arrive to the job site 226. In this embodiment, once they arrive the computer hub manager 230, using any kind of computer like a laptop, personal digital assistant (PDA) like a tablet computer or even a cell phone, would be able to complete the assignments of computer hub 216b to electronic assets 220c, 220d on site 226.

Figure 5:
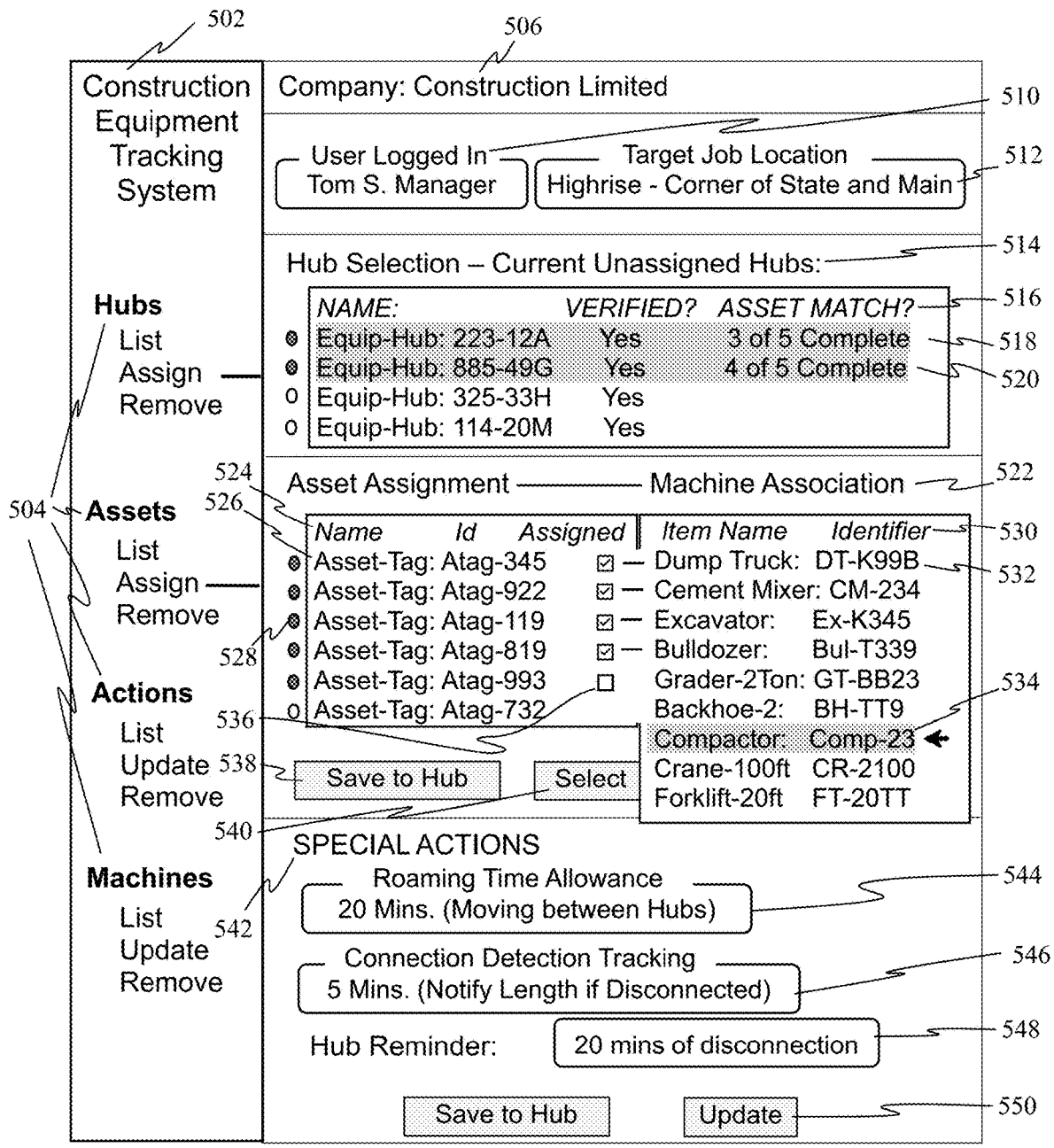
FIG. 5 is another embodiment for an interface on a central server for selecting and directing the operation of one or more computer hubs.

As illustrated by FIG. 5, once the computer hub manager 230 is logged into the central server 202 they can begin selecting one or more computer hubs 216 they want to work with. They are then provided a list of one or more electronic assets 220 that are not currently assigned to be assigned to the one or more computer hubs 216 selected. During this assignment of computer hubs 216 and electronic assets 220, the computer hub manager 230 can select another item name and identification number to help define the nature of the electronic asset 220 and what exactly it will be associated to. In this way if a computer hub manager 230 receives a message from a given computer hub 216 related to a electronic asset 220, they will know that a specific item on the job site has gone missing.

In this embodiment to deal with the size and scope of the job site and the potential limited range of the electronic assets 220 radio frequency coverage, multiple computer hubs 216b can be used on the job site 226 to cope with movement of equipment on the job site 226. At any time if an electronic asset 220c, 220d cannot connect with one computer hub 216b, it will try other computer hubs 216b that it has in its list of associated computer hubs 216b. This means the computer hub manager 230 will have to progressively couple each of the one or more computer hubs 216a, 216b to each of the assigned electronic assets 220a, 220b, 220c, 220d. This way the electronic assets 220a, 220b, 220c, 220d will be able to seek out and connect with any of the computer hubs 216a, 216b it has been originally coupled with.

Figure 3:
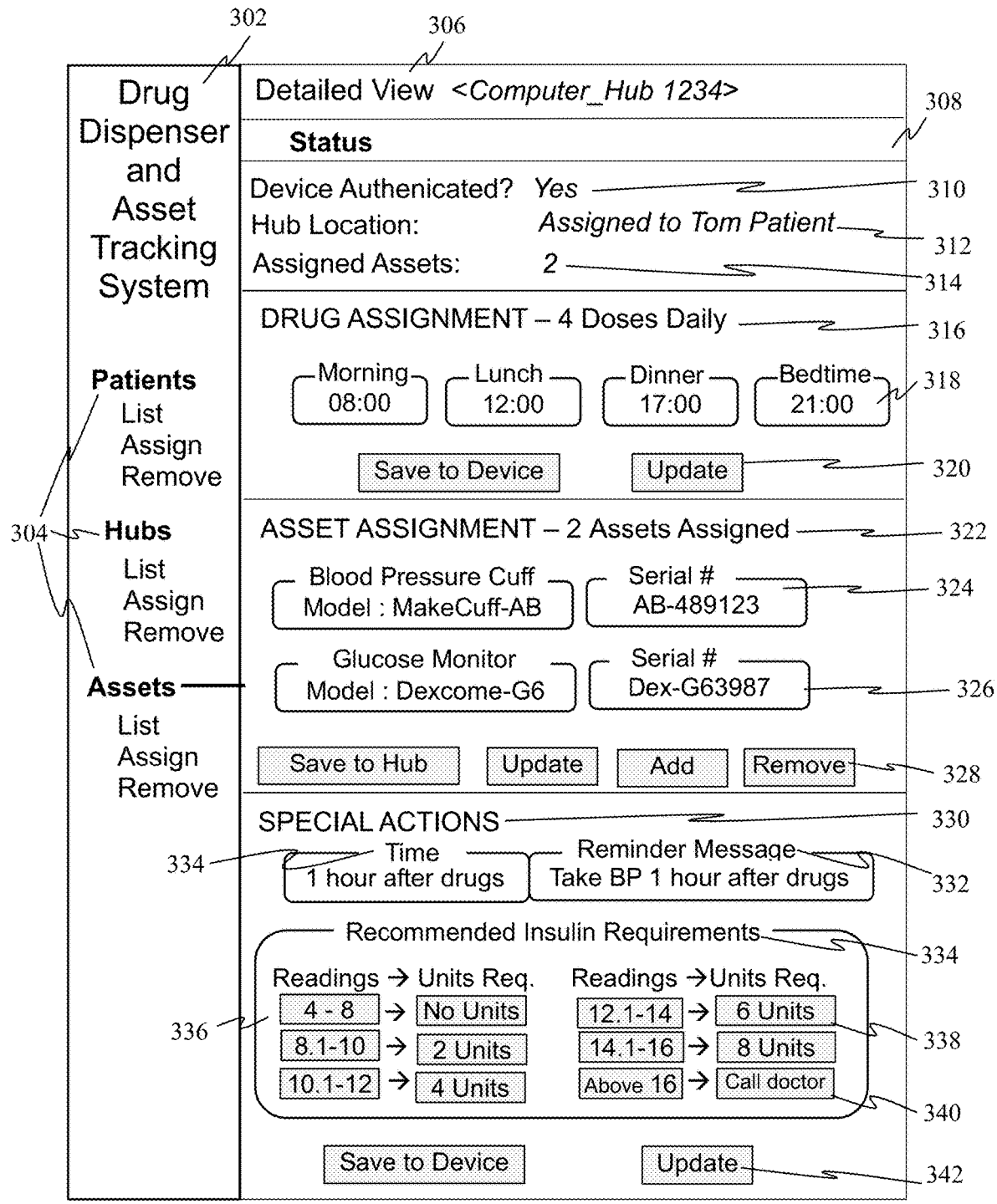
FIG. 3 shows an example embodiment for an interface on a central server for selecting and directing the operation of one or more computer hubs.

Moving to FIG. 3 there is shown a first embodiment for a user interface (UI) 302 on a central server 102 for selecting and directing the operation of one or more computer hubs 116. This first embodiment illustrates a system where the computer hub 116 is both a medication computer hub and an asset tracking system.

There are many possible embodiments for a UI 302 on a central server 102 to guide the listing, assigning and managing of computer hubs and their associated electronic assets. This illustration 302 represents a simplified single view of a configuration screen that explains the process in general for the computer hub manager 130. It is not meant to limit in any way all the myriad of other alternative visual approaches and alternative configuration settings that would be possible. Advanced use of mouse movements, hoover effects, drop down menus that dynamically change are all possible their use can allow for even further implementations.

The selected title for this configuration screen 302 is Medication Dispenser and Asset Tracking System. In other embodiments it could also be call Computer Hub Management Screen or many other such titles. For illustration three sections 304 are represented in this screen. These sections 304 include the Patients section, the Hubs section and the Assets. In other embodiments there could be additional sections for administrators to grant permissions to computer hub managers 130, sections for adding and removing patients and many more. In this illustration the computer hub manager 130 has listed all the available computer hubs 116 and have selected one computer hub 116 to view the detailed information 306 for.

This detailed view 306 is for computer hub 116 number 1234. The Status section 308 is illustrated first and it indicates whether the device has been authenticated by the computer server 310. Without authentication the computer hub 116, in this example number 1234 could not be used and would not be capable of sending and receiving messages to the central server 102. The assignment location for this computer hub 116 is currently with a patient, whose name is Tom Patient 312. This computer hub 116 also has two assets 120 assigned to it based on assignments made by authorized computer hub managers 130.

The second section illustrated the medication assignments for this medication dispenser 316. The medication regimen assigned is for 4 daily doses 316. These four times are morning at 8:00 am, lunch at 12:00 pm, dinner at 5:00 pm and bedtime at 9:00 pm 318. Once all the necessary changes are made to this area the computer hub manager 130 can save them to the computer hub 116 or update them further 320. Saving them to the computer hub 116 effectively sends them over one or more networks 110, 112 to the computer hub 1234 (116).

The next section in this embodiment shows the asset assignment section 322. Currently there are two electronic assets 120 assigned to this computer hub 116. The first electronic asset 120 is a blood pressure cuff, model Make-Cuff-23B and with a serial number of AB-489123 (324). The second electronic asset 120 is a Glucose Monitor, model Dexcome-G6 and with a serial number of Dex-G63987 (326). Using this section, the computer hub manager 130 can save these assignments to the computer hub 116, they can update the assignment, add new electronic assets 116 or remove electronic assets 116 (328). Each of these changes would cause a message to be exchanged with the computer hub 116 to confirm the addition or removal of electronic assets 120.

The final section in this embodiment shows the special actions 330 that should be taken when using the computer hub 116. There are many potential special actions 330 but in this embodiment there is an example of sending a reminder message to the patient to take their blood pressure 1 hour after medications are taken 332. This message is complemented with a specific control directive to the computer hub 116 telling it to run a one-hour timing to generate a reminder sound or action on the computer hub 116 (334).

The second example is supported by the control directives only when a blood glucose type electronic asset 120 is configured and connected to the computer hub 120. In this embodiment a computer hub manager 130, probably a licensed pharmacist, is reading a chart of blood glucose readings and recommended insulin injections that have been prescribed by an endocrinologist.

To complete this part of the recommended insulin requirements 334, they 130 simply enter the readings 336 and the corresponding units required 338 from the doctor's prescription. In some cases they are given a drop-down list of selections that allow specialized strings like: 'call doctor' 340. The readings are in millimoles per litre and the units are graduated on the insulin pen to ensure accuracy. Once they 130 have completed the form and all the fields, the control directives are generated that can guide the patient 134 as to how much insulin to inject. Based on the reading provided by the glucose monitor the display on the computer hub 116a could display the exact reading received from the computer asset 116 and remind the patient 134 exact what the doctor suggested they do to support that level of blood glucose. These readings and levels can be changed at any time and a new set of control directives given to the computer hub 116a.

In another embodiment, the computer hub manager 130 has also attached a Bluetooth enabled insulin pen to the same computer hub 116a. In this embodiment a command could be sent from the computer hub 116a to the insulin pen 116 telling it exactly the number of units that should be injected. For an patient with mobility issues, or mental deficiencies this would remove any chance of error on the part of the patient 134.

These special actions 342 can then be saved to the computer hub 116 or further updated with additional reminders and timer actions 336. In other embodiments for example the action might require alternative between blood pressure and weight scale readings several times a day. Many potential special actions 330 could be configured for this computer hub 116.

Figure 4:
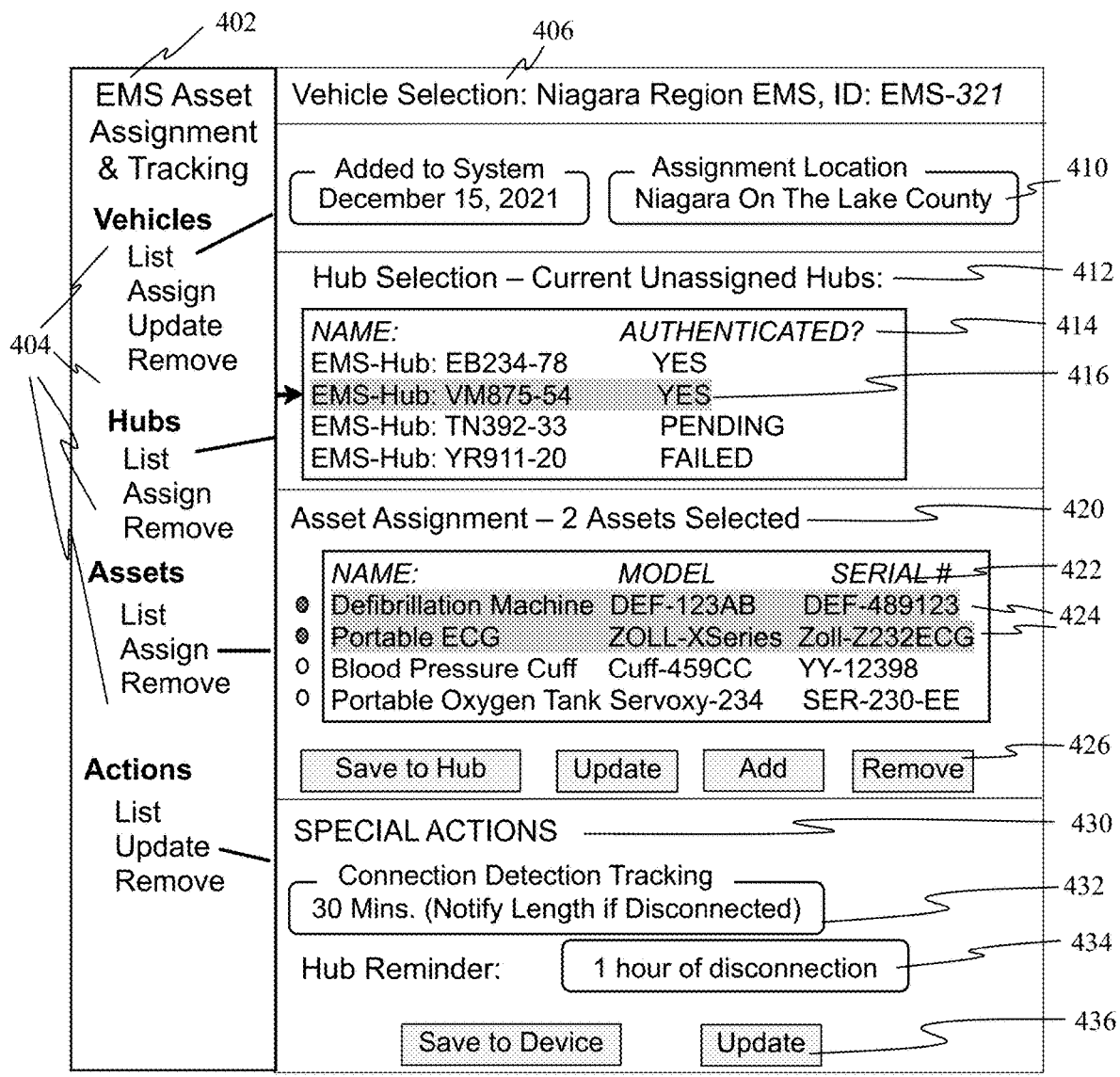
FIG. 4 shows another example embodiment for an interface on a central server for selecting and directing the operation of one or more computer hubs.

FIG. 4 shows a second embodiment 402 for a user interface 406 on a central server 102 for selecting and directing the operation of one or more computer hubs 116. This second embodiment illustrates a different method where a computer hub 116 is selected and one or more computer assets 120 are assigned for tracking purposes. In this embodiment the computer assets 120 relate to an emergency medical service (EMS) vehicle, hospital location, medical laboratory or any other facility that has many moveable electronic assets 120.

The figure shows an example of an EMS Asset Assignment and Tracking System 402 main screen, with an assignment being made to the current vehicle selection Niagara Region EMS, ID: EMS-321. There are many possible embodiments for a UI related to EMS asset assignment and tracking 402 and this illustration is a simplified example to illustrate the flexibility of a method for selecting, associating, managing and tracking electronic assets 120 by a computer hub 116.

There are several different broad areas the computer hub manager 130 can work with 404. Since this embodiment is focused on EMS and vehicle support the first main area is for Vehicles 404. All vehicles to be supported by the system have been entered into the central server's 102 database 106. The computer hub manager 130 can list, assign, update (add) and remove vehicles 404 from the central server 102. They can also perform similar actions on computer hubs 116, electronic assets 120 and on actions which relate to the control directives around how to treat different electronic assets within the computer hub 116.

The list display for Niagara Region EMS, ID: EMS-321 shows that it was added to the system on Dec. 15, 2021 and it's current location is Niagara on the Lake County 410.

The list display for the Hub Selection 412 shows a list of currently unassigned computer hubs 116 at the central server 102 (412). If the current status of a computer hub 116 is authenticated=Yes 416 it means that it is capable of exchanging secure messages with the central server 102. The user 130 has selected EMS-Hub: VM875-54 to assign to the EMS vehicle identified as EMS-321 (416). This computer hub 116 shows a status of fully authenticated 416, while some of the other computer hubs 116 shows a status of Pending and Failed.

The asset assignment tab 420 shows 2 electronic assets 120 have been selected and assigned 424. The title line 422 provides the name, model and serial number of each electronic asset 120 so that the correct units will be selected and placed into the EMS vehicle EMS-321. The first electronic asset 120 selected is a defibrillator machine model number DEF-123AB with serial number DEF-489123 (424). The second electronic asset 120 is a portable ECG machine, model number ZOLL-XSeries, Serial number Zoll-Z232ECG (424). The interface also allows the user to Add, Remove, Update and then Save this information to the computer hub 426.

The special actions section 430 allows the user to adjust how each of the electronic assets 120 are tracked and managed 430. These represent one embodiments of control directives to guide the computer hub 116 when dealing with electronic assets 120.

In this embodiment the user has added connection detection tracking of 30 minutes 432. This means that if the electronic asset 120 is disconnected for more than 30 minutes a message is sent by the computer hub 116 to the computer hub manager 130 to inform them that something needs to be checked. On the computer hub 116 itself the user has configured a computer hub 116 reminder of 1 hour for the same disconnection 434. In this embodiment this different in time might allow the computer hub manager 130 to know ahead of time when the electronic asset 116 is missing should a rogue employee be trying to steal or misappropriate the electronic asset 120 for their own personal use. Once entered this control directive information can be saved to the computer hub 116 or updated further 436. These control directives can also be updated at any time 436 and resent to the computer hub 116 as needed.

Other embodiments are possible in all the sections for the computer hub manager 130. There could be control over how the GPS is used, notifications should the electronic assets 120 and the computer hub 116 extend out of a certain geographic region. There could be embodiments to require the electronic assets 120 are returned each day or week at the end of a shift to be accounted for. This might generate messages and notifications on the computer hub 116 to remind the EMS drivers to perform these steps. In other embodiments there could be controls for turning them off to preserve battery life, reminders to push buttons to perform specialized readings and many others. Many embodiments are possible with the flexibility of the interface to provide many different types of control directives to the computer hub manager 130.

Turning to FIG. 5 there is another embodiment for a user interface 502 on a central server 202 for selecting and directing the operation of one or more computer hubs 216. This embodiment is focused on the tracking and management of construction equipment 502 in a construction company called 'Construction Limited' 506. Although this embodiment is focused on construction and construction vehicles, it could apply to any industry where items they own need to be tracked in a confined area.

This UI illustration shows a Construction Equipment Tracking System 502 with a series of different areas 504 for the computer hub manager 230 to work with. They can look at computer hubs 216 by listing them, assigning them and removing them from the system. They can also look at electronic assets 220 and list them, assign them or remove them. They can set up control directives in the Actions section by listing, updating, and removing different sets of actions. Finally, the computer hub manager 230 can work with the company's machines and list them, update them (add them) and remove them from the system.

For the current operation the user logged in is Tom S. Manager 510, there could be many different computer hub managers 230 all with different roles, job site controls and responsibilities. This could be setup by the IT department following guidance from the senior management of company Construction Limited 506. The target job location for the computer hubs 216 and electronic assets 220 is the highrise at the corner of State and Main 512.

In the hub selection area 514, is a list of all current unassigned computer hubs 216 available for assignment for this job site. The interface shows the computer hub manager 230 has selected two hub 518, 520. The title line provides information about the name, verification status and asset match 516. This is useful as the name allows the computer hub manager 230 to grab the correct computer hub 216 for assignment. The verified status indicates whether it is authenticated or not, the previous UI example used the word authenticated but in this UI the word verified is used 516. Finally, the asset match 516 indicates that of all the electronic assets 220 assigned to this job site that a certain number have been coupled to the computer hub 220.

Depending on the embodiment and communication medium used, the process of coupling all the selected electronic assets 220 to the selected computer hubs 216 will take a certain amount of work. If a RF technology like Bluetooth was being utilized, then the computer hub manager 230 will have to progressive turn each of the selected computer hubs 216 on and select each electronic asset 220 to couple to that computer hub 216. Then once complete, they would turn the computer hub 216 off and do the same with all the other electronic hubs 216 assigned to the same job site. In this way the computer hub 216 and a given electronic asset 220 with the strongest signal combination will naturally pair first and repair with other computer hubs 216 as the signal strength changed.

In this illustration the two computer hubs 216 selected are Equip-Hub identifier 223-12A (518) and Equip-Hub identifier 885-49G (520). The first computer hub 518 has just 3 of 5 selected electronic assets matched and the second computer hub 520 has 4 of 5 selected electronic assets matched.

Moving to the asset assignment and machine association area 522 we can see that there are five different electronic assets 220 selected 528. The label 524 provides the name, identifier and assigned status. The assigned status indicates that it has been assigned to a specific piece of equipment in the company's equipment database of construction items. In other embodiments with lots of screen space it would also be possible to list exactly which coupling of electronic assets 220 to computer hub 216 had been completed. For this example the UI only shows the total count 518, 520 of coupled electronic assets 220 to selected computer hubs 216.

The first box in the asset assignment section 522 provides a pick list of all known and available Asset tags 526 in this embodiment. Each asset tag has an identifier and in this example the asset tags Atag-345, Atag-922, Atag-119, Atag-819 and Atag-993 have all be selected 528 for this job site 512. The first four have been assigned with a company item and the fifth is still pending an assignment 536. The checked boxes indicate the assignment is complete while the open box 536 indicates that the computer hub manager 230 has one more to complete.

The other box in the asset assignment section 522 provides a pick list of all known company items 530 they wish to have tracked and managed. The title 530 indicates the item name and any identification the item might have. For example in some embodiments this could be a model number, serial number or a specially attached label to ensure that each item can be uniquely identified for the purposes of assignment and tracking.

In this illustration, the user 230 of this interface would be provided a long pick-list of all the known items that have been entered into the companies equipment database 206. The first four have already been locked into place and a line indicates which electronic asset 220 they have been assigned to. In this example the user 230 is currently scrolling through the list and is sitting on item name compactor with identifier Comp-23 (534). The arrowhead is used to help the viewer identify where they are sitting on the list. When they are happy with the selection, they can pick the select option 540 and the assignment is locked into place. Other options not shown in this illustration would allow the assignment to be updated, removed or changed. Once all the assignments are complete the list of electronic asset 220 assignments can be saved to the selected computer hubs 538 for further action.

In the final special actions section 542 the computer hub manager 230 can set up control directives to guide the actions of the computer hub 216 with respect to one or more of the electronic assets 220. In this illustration the special actions are applied to every electronic asset 220, but in other embodiments there could be a different set of control directives established for each individual electronic asset 220. For example, it might be important for the electronic assets 220 associated to very high-priced items, like a 100-foot-high crane, to have a minute-by-minute timer for connectivity status. In another example, a dump truck might be given a 2-hour disconnect window so it can take different loads of gravel too or from the construction site.

In this example, the computer hub manager 230 has decided that he will allow for a 20-minute roaming allowance time 544. This means that if a piece of equipment is allowed to be out of contact for 20 minutes as it moves between locations and between different computer hubs 216. This might be a common length of time on a large construction site. However, after this 20-minute window or at any other time only 5 minutes are allowed for a disconnection event. If after 25 minutes (20 roaming+5 disconnected) the electronic asset 220 has not reconnected with one of the computer hubs 220 an alarm is raised in the central server 202 and is relayed onto the computer hub manager 230. Locally on the computer hub 216 the hub reminder is set to 20 minutes after disconnection 548, a total of 20+20 or 40 total minutes of disconnection. This difference could give the computer hub manager 230 time to react before a rogue employee tries to steal a piece of equipment.

When completed any control directive changes the computer hub manager 230 can then save this information to the hub 550. They can also return to this area and update 550 any of the control directives as needed.

Figure 6:
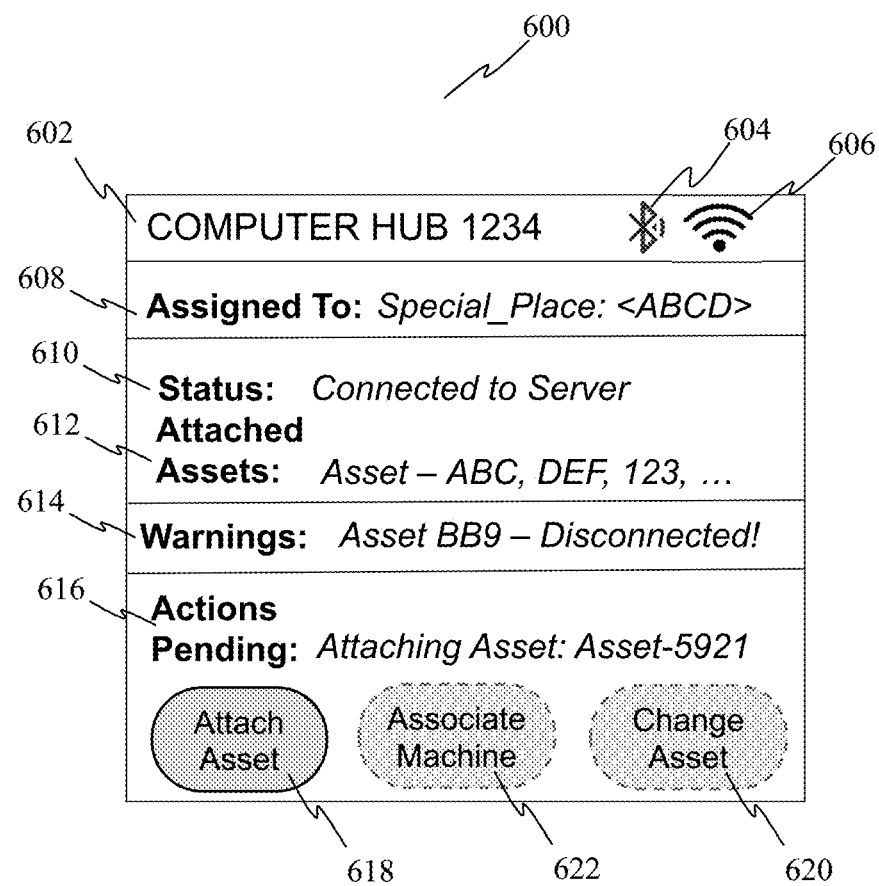
FIG. 6 shows an embodiment of an interface on a computer hub for directing and connecting electronic assets.

FIG. 6 shows an embodiment of a user interface 600 on a computer hub 116 for directing and connecting electronic assets 120. This embodiment illustrates a system 100, 200 where the computer hub 116, 216 is used within different embodiments. Some of the embodiments discussed thus far have been operating within a drug dispensing computer hub 116*a*, a computer hub 116*b* operating within an emergency response vehicle 136, and as a computer hub 216 within the construction industry all involving electronic asset 120, 220 that need to be tracked and monitored. There are many other embodiments where the computer hub 116, 216 might be suited, and different UIs that would be better suited on the computer hub for those environments. This illustration is not intended to limit or infer that many other UIs would not also be well suited to a computer hub.

There are many possible embodiments for a UI 602 on a computer hub 116, 216 to guide the detecting, attaching, and monitoring of electronic assets 120, 220. This illustration 602 represents a simplified single view of a status screen that explains the process in general for the local user 134, 138, and computer hub managers 130, 230 to use when interacting with a computer hub 116, 216. It is not meant to limit in any way all the myriad of other alternative visual approaches and alternative status and informational displays that would be possible. Advanced use LED illumination, warning lights and sounds, LED screens with both colour and monochrome offer many advanced alternative embodiments.

The embodiment shown is for the computer hub number 1234 (602). The status line shows a short-range RF signal indicator 604 and a wide-area RF signal indicator 606. These are present to help guide the user of the computer hub 116, 216 to ensure communications are working correctly. In other embodiments an indicator should be shown for a physical connection, like USB or even a NFC connection.

The first status line shows the computer hub 116, 216 is assigned to a 'Special_Place <ABCD> 608. This line is a status line to keep anyone interacting with the computer hub 116, 216 informed as to what its current assignment is. This also tells the computer hub manager 130, 230 that this computer hub 116, 216 is current unavailable for assignment to another location or activity.

The next status shows that the computer hub 116, 216 is currently connected to the server 610. This effectively means that electronic asset 120, 220 assignment messages, control directives and other types of confirmation messages can be exchanged, including any readings from connected electronic assets 120, 220. In this example there are several attached assets 612 being displayed at the moment, for this illustration kept generic as Asset ABC, DEF, 123 and others 612.

The next section of the UI display shows there is one warning currently outstanding 614. This warning 614 indicates that one electronic asset BB9 is currently disconnected. This means the control directive maximum disconnect time must have been reached for this electronic asset 120, 220. It might also display that the vehicle is moving and an electronic asset 120, 220 is not currently within range. Meaning that even though its disconnection timer has not expired, the movement of the vehicle has triggered a warning to the user to check for all electronic assets 120, 220 that are not currently within range and are disconnected.

The lowest status area 616 indicates that there is one action pending. In this example the action 616 is to attach the Asset-5921 (616). To attach the electronic asset 5921 the user can select the Attach Asset 618 button. If permitted by the central server 102, 202 they might be able to select the Change Asset button 620. This might allow them to disconnect or modify (swap) an electronic asset 120, 220 should the one they are using start to experience issues and problems. As they connect new electronic assets 120, 220 the upper status area 612 will be updated to display all electronic assets 120, 220 connected. In some embodiments there could also be other buttons like an Associate Machine 622 button to perform a unique connection action with a machine. This type of coupling might allow power-on readings to be taken, travel time to be collected and other important information.

Figure 7:
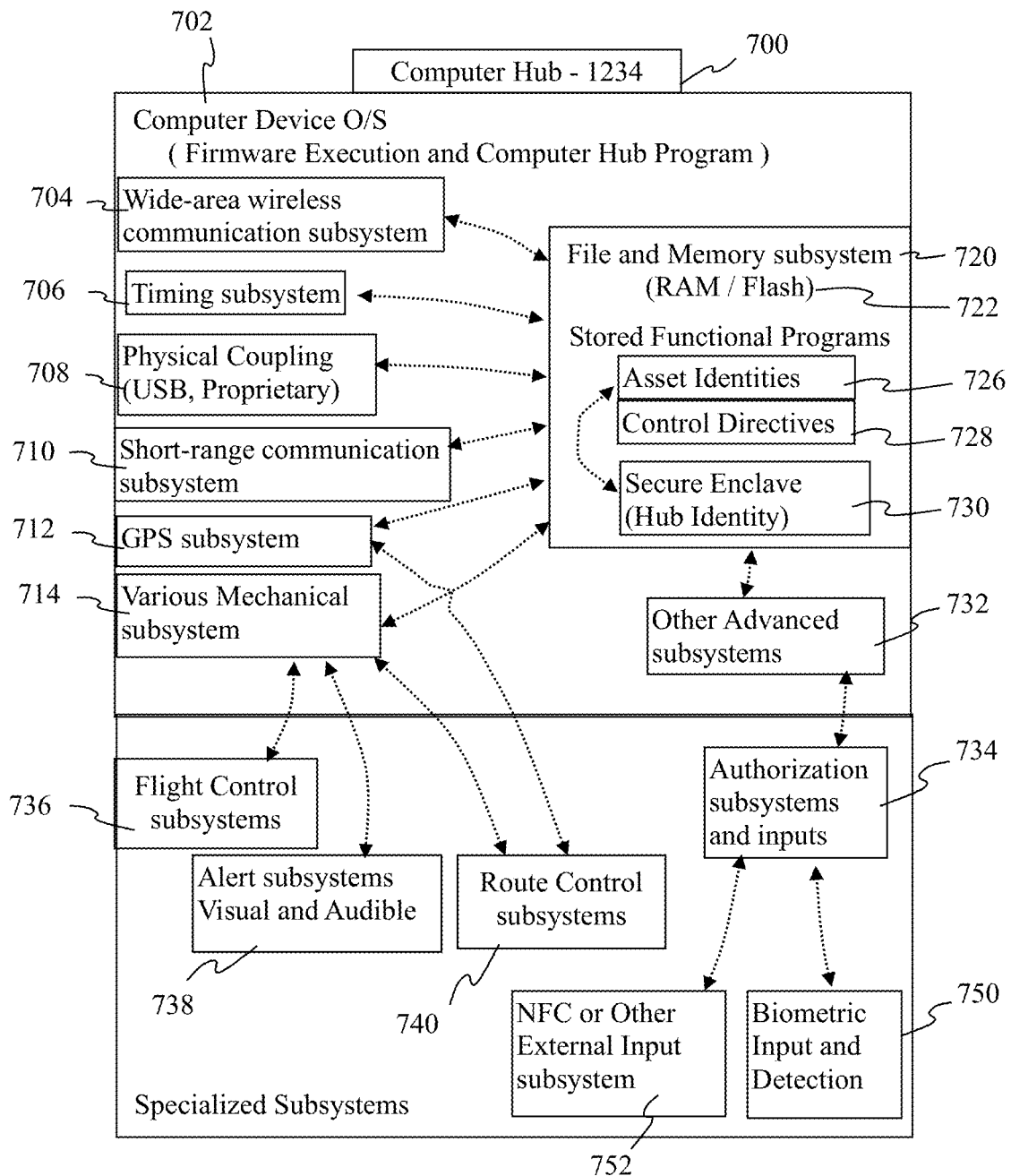
FIG. 7 shows an embodiment for internal elements of a computer hub.

Turning to FIG. 7 there is an illustration showing an embodiment for internal elements of a computer hub identification 1234 (700). There are many potential embodiments with a range of potential internal components depending on function and form and overall purpose. A medication dispensing machine that is also a computer hub 116*a* might have more mechanical motors, gears and dispensing components for example.

The computer hub 700 is running a controller piece of software 702, called a Computer Device O/S (operating system), in this illustration. This could be an embedded O/S 702 like FreeRTOS (Free Real Time Operating System), or many other O/S choices. In some embodiments this software 702 could also be referred to as firmware or the computer hub 116 program running on an embedded device. The O/S and firmware 702 provides interface methods to a series of sub-systems available for use by one or more programs trying to control the computer hub 700. In one embodiment these sub-systems could be reached using application program interface (API) calls. In other embodiments these sub-systems can be linked directly to programs loaded onto the computer hub 700. In some embodiments these sub-systems are connected on a printed circuit board (PCB) and are connected electrically together. The illustration 700 is provided as an example of one embodiment and other possible sub-systems could be included in other embodiments.

For example, within the mechanical sub-system 712 could be further specialized sub-systems, like a flight control sub-system 736, alert sub-systems with visual and audible alarming capable capabilities 738 and route-control sub-systems 740 to name just a few alternative and specialized sub-systems. These and many other specialized features might be present when the computer hub 700 is designed and manufactured.

The first sub-system listed is the wide-area wireless communication sub-system 704. This sub-system would be used to reach one or more external radio towers capable of radio frequency communications. This communication method would be focused on exchange of data with the central server 120. This would be used for delivery of the computer hub 116 identity 726, for electronic asset 120 connection attempts, tracking and information messages to name just a few. It might also server for receiving control directives 728 from the central server 102 and other types of commands for connecting and disconnecting electronic assets 120. There are many different embodiments for wide-area communication methods like GSM, GPRS, UMTS type system and IEEE.11 (WiFi) type communication methods to name just a few.

The next sub-system illustrated is the timing sub-system 706. The timing sub-system 706 might allow for programs to set timer alarms and be notified when the timer expires. Such timers are often used to indicate the passage of time to detect key events, for example whether an electronic asset 120 is still connected, or whether it is time to acquire a reading from a connected electronic asset 120. In other embodiments the timer sub-system 706 might also indicate that it is time for another medication dose by a consumer 134.

The next communication method shows would be a sub-system for physically coupled electronic assets 708. This could include serial connections, universal serial bus (USB) connections, RJ11 connections and many other proprietary physical links. In other embodiments this could connect many other physical types of devices like RFID readers, RFID scanners, barcode scanners and others in addition to electronic assets 120.

The next subsystem shown is for using different short-range wireless communication methods to communication 710 to local electronic assets 120. This might include Bluetooth, NFC, WiFi, other types of proprietary cellular communications. This subsystem 710 might support just one or many of these types of communication methods for the computer hub. The short-range communication subsystem 710 could also be used for other types of connections like Bluetooth RFID readers and scanners, Bluetooth lights, doorbells, alarms and many others.

The next sub-system is the GPS sub-system 712 which would be used to retrieve the current GPS co-ordinates on the globe. In some embodiments the computer hub 116 uses the GPS co-ordinates to determine when movement is taking place to trigger a check on all available and connected electronic assets 120. In other embodiments the GPS co-ordinates might also be sent along with every electronic asset 120 reading to the central server 102 for further detailed information on where a given electronic asset 120 reading was taken.

The next sub-system is collection of mechanical subsystems 714 linked to specialized subsystems based on the type of computer hub 116 that is being utilized. In one embodiment, these could include flight control subsystem 736, an alert subsystem 738, and route control subsystems 740. In other embodiments there could be smart patch detection subsystems and many others. The mechanical subsystem 714 would be designed to provide control to physically moving parts, for example in embodiments with pill dispensing required. It could also support LED screens, lights and auditory supports in the computer hub 116 for helping interface to the local user 134, 138. In different embodiments these mechanical subsystems 714 might be used to support a self-driving VTOL, taxi or EMS type vehicle.

The File and memory subsystem 720 is the next subsystem shown and is used to store and retrieve information which is local to the computer hub 116. The memory subsystem 720 could be constructed with different random access memory (RAM), read-only memory (ROM) and Flash memory type chip configurations. The use of these different memory options 722 allow for different types and configuration of file systems 720 to support the various programs running in the computer hub 116. Stored functional programs can also be saved within slower access Flash memory and moved into faster-access RAM memory to increase speed and performance of the computer hub 116.

Within the memory subsystem 720 will be specialized models like secure enclave 730 memory systems. These secure enclave memory systems 730 might be used to safely store computer hub identities 730 to ensure they are tamper proof and known only by the central computer 102. This memory 730 might also hold public/private encryption key pairs that are generated at manufacturing time.

Other memory might be used for storing electronic asset identities 726 and control directives 728 as received from the central computer 102. Placing these in permanent non-transitory memory ensures the information can be retained across power loss and any major disruptions.

Other specialized subsystems can include authorization subsystem 734 for supporting different forms of authorization detection. In one embodiment, the authorization sub-system 734 utilizes the Biometric Input and Detection subsystem 750, which is used to accept bio-identification from a computer hub 116 users. In other embodiments the authorization subsystem 734 might utilize an NFC input subsystem or other proprietary or specialized types of authorization methods. For example, a specialized reader might be used to detect and read sub-dermal implants that are placed under the skin of the intended computer hub user. This computer hub user might be an EMS driver, a medication consumer, a homeowner, an owner of a self-flying VTOL or self-driving taxi or many other embodiments. Depending on the design and chip set used within the PCB, the type of authorization identity 734 used could vary from one computer hub 700 to another computer hub 116. In some embodiments the authorization sub-system 734 might also include biomedical input options for collecting blood, DNA, urine or other bodily attributes to verify the user.

In some embodiments different external input subsystems 750 might exist to provide additional specialized links to external equipment. This additional external equipment might allow even more input about the user. For example, in some embodiments there could be EKG monitors, blood pressure readings, heart rhythms detectors and many others for identifying users. There could be also fingerprint readers, deep palm scanners or even retinal scanners. In some embodiments a sub-dermal implant could be read using an RFID scanning method (NFC) to power up and scan the identity of an individual.

Once installed within the O/S or firmware the computer hub program 702 provides oversight to the operation of the computer hub 116. The computer hub's 700 basic operation starts and ends as controlled by the computer hub program 702. This program 702 might start in flash memory 722 and move into RAM or run solely within the flash memory.

There are many embodiments for how this program 702 might operate. In some embodiments, it 702 informs the user 134, 138 when electronic assets 120 are allowed to be connected, how to connect them and then monitors them for an indefinitely period of time. In some embodiments, the computer hub 116 also involved with pill dispensing operations, vehicle transportation, vehicle flight, home safety protection and other jobs.

In some embodiments, the computer hub program 702 also detects the removal or absence of electronic assets 120 in real-time, using short-range communication methods. There are also secure and robust tamper-proof memory solutions to hold sensitive and private information including but not limited to computer hub identities 730, electronic asset identities 726 and control directives 728. Another key goal of the computer hub program 702 is to use the control directives to provide automatic and timed based event tracking for reading data from electronic assets 120. Such readings can provide vitals on patients, security in a home, health of passengers in a self-driving mode of transportation and many other embodiments. These tracking messages are then relayed to the central server 102 using wide-area communication methods to ensure one or more computer hub managers 130 are informed in a timely fashion. When available, messages about current location from the GPS sub-system 712 would be valuable to understand where computer assets 120 are located, where electronic asset 120 are acquired and other similar useful correlated information.

There are many other algorithmic procedures that are possible within all the subsystems that are available on the computer hub 700. For example, there could be additional tamper detection subsystem for sensing if anyone is tampering with one or more of the electronic assets 120. These tamper-detecting subsystems might send alarms to the computer hub program 702 to relay onto the central server 102. These any other embodiments could be present to perform advanced functions 732.

In one embodiment there is a subsystem 750 to interact with a wearable device that detects whether the user 134, 138 has left the premises of the computer hub 700. In some embodiments the user 134, 138 is required to be close to, watching and protecting the computer hub 116 at all times. These and many other embodiments are possible with additional subsystems and functional design goals.

In other embodiments the external input subsystem 750 allows coupling to a machine to reach power-on readings or movement readings for a machine or item that is being tracked using the electronic asset 120, 220.

Figure 8:
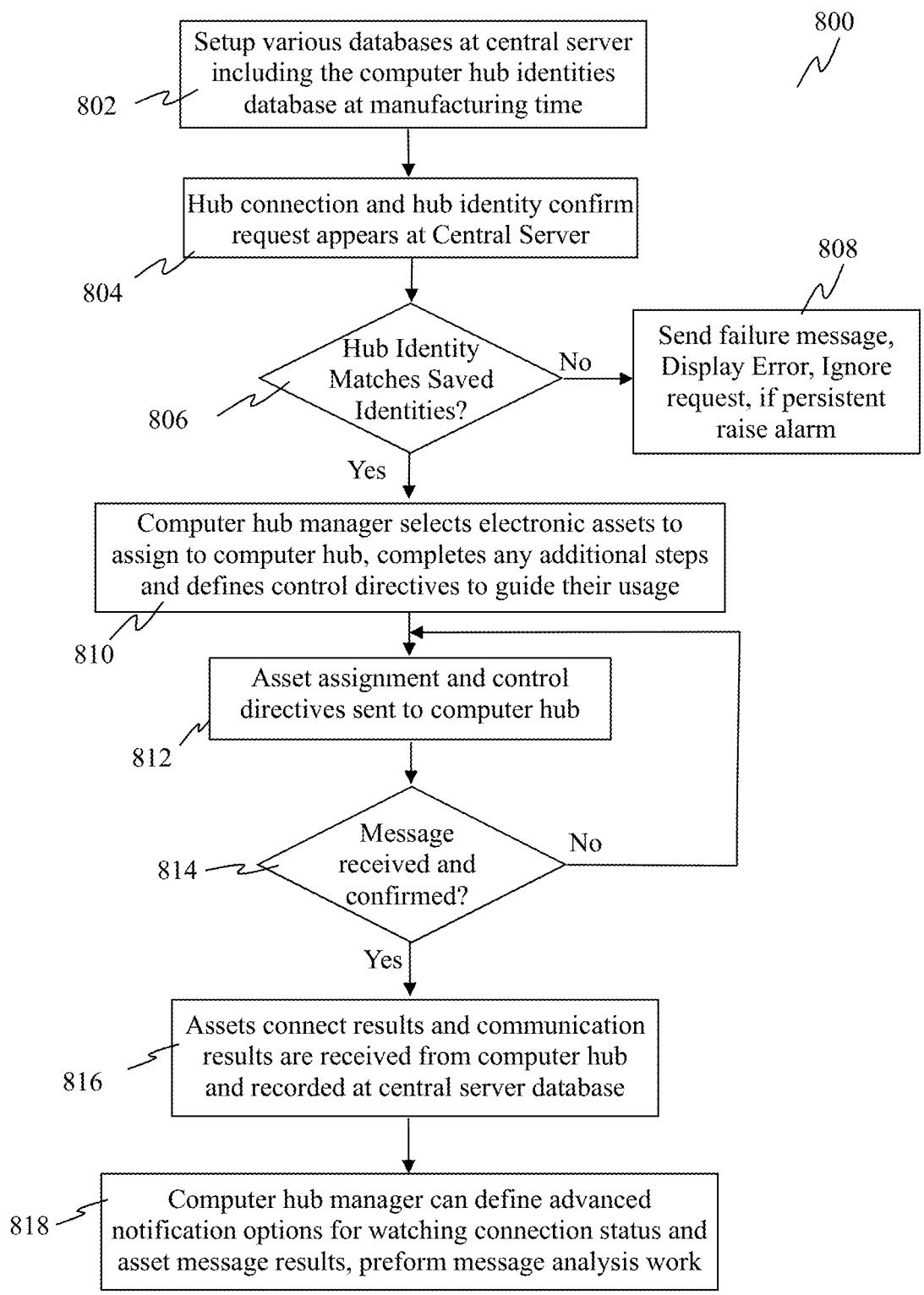
FIG. 8 shows a data flow diagram for an embodiment of the steps taken by a computer hub manager at a central server.

FIG. 8 shows a data flow diagram 800 for one embodiment of the steps taken by a computer hub manager 130 at a central server 102, 220. This data flow diagram 800 provides one embodiment for important steps when setting up computer hubs 116, 216, but there are many other embodiments which could include additional steps.

In this embodiment, the first step illustrated is for the central server 102, 202 to establish the various databases 106, 206 at the central server 102, 202 in some embodiments. This might include drug (or medicine) dispensing machines, fleets of EMS vehicles, ambulance vehicles, VTOLs, self driving taxis or inventories of construction machines or other kinds of machines to name just a few. This setup includes a database 106, 206 of computer hub identities 802. As discussed earlier, this could be performed during manufacturing, either using encryption keys or a direct connection that exchanges the hub identity within a closed and secure environment, i.e. a manufacturing plant.

The next step is when the computer hub 116, 216 tries to connect and sends its hub identity to the central server 102, 202 for confirmation 804. If the hub identity does not match 806 then an error is sent to the requesting computer hub 116, 216, an error message is displayed on the central server 102, 202 UI, and the request is ignored 808. If this type of error persists an alarm could be raised to the administrator who oversees all of the computer hub managers 130, 230. The computer hub manager 130, 230 will have to retire that computer hub 116, 216 and get another one that is considered still valid. It is possible a rogue computer hub 116, 216 has been slipped into the batch of authentic ones or a rogue agent is trying to hack the central server 102, 202.

If the hub identity matches a value in the database 806 then the computer hub manager 130, 230 can then select electronic assets 120, 220 to assign to this computer hub 116, 216 and they also define control directives for each of these electronic assets 810. These asset assignments and control directives are then sent to the computer hub for execution 812.

The central server 102, 202 then waits for a message to confirm the reception of the electronic asset 120, 220 assignments and the control directives 814. If they are not received the message could be resent 812, until some form of confirmation is received.

Eventually the computer hub 116, 216 confirms the electronic asset 120, 220 assignment and the control directives 816. This confirmation is recorded by the central server 102, 202 into its database 106 as it can be considered a permanent assignment 816.

Finally, the computer hub manager 130, 230 can add advanced notifications and make additional changes to all areas of the configuration through the UI 818, they could even come back again and again to make changes, check on readings, connection results and check alerts. During this operation period the central server 102, 202 is receiving information from both the computer hub 116, 216 and the one or more electronic assets 120, 220 connected to that computer hub 116, 216. In some embodiments, when the computer hub 116 also has its own internal operation like drug (or medicine) dispensing, information can be interlaced and correlated. For example, statistical analysis can be used on consumption of drugs and readings of vital signs from various electronic assets 120. The arrival of all this data allows for statistical operations to be performed, advanced predictive analysis as well, leading in artificial intelligence algorithms to assist with better effects of drug consumption on a person's bodily functions like heart pressure, arrhythmias, blood sugar levels and many other types of bodily readings. Embodiments described herein can be used for management of devices or electronic assets related to drugs or medicine, for example.

Figure 9:
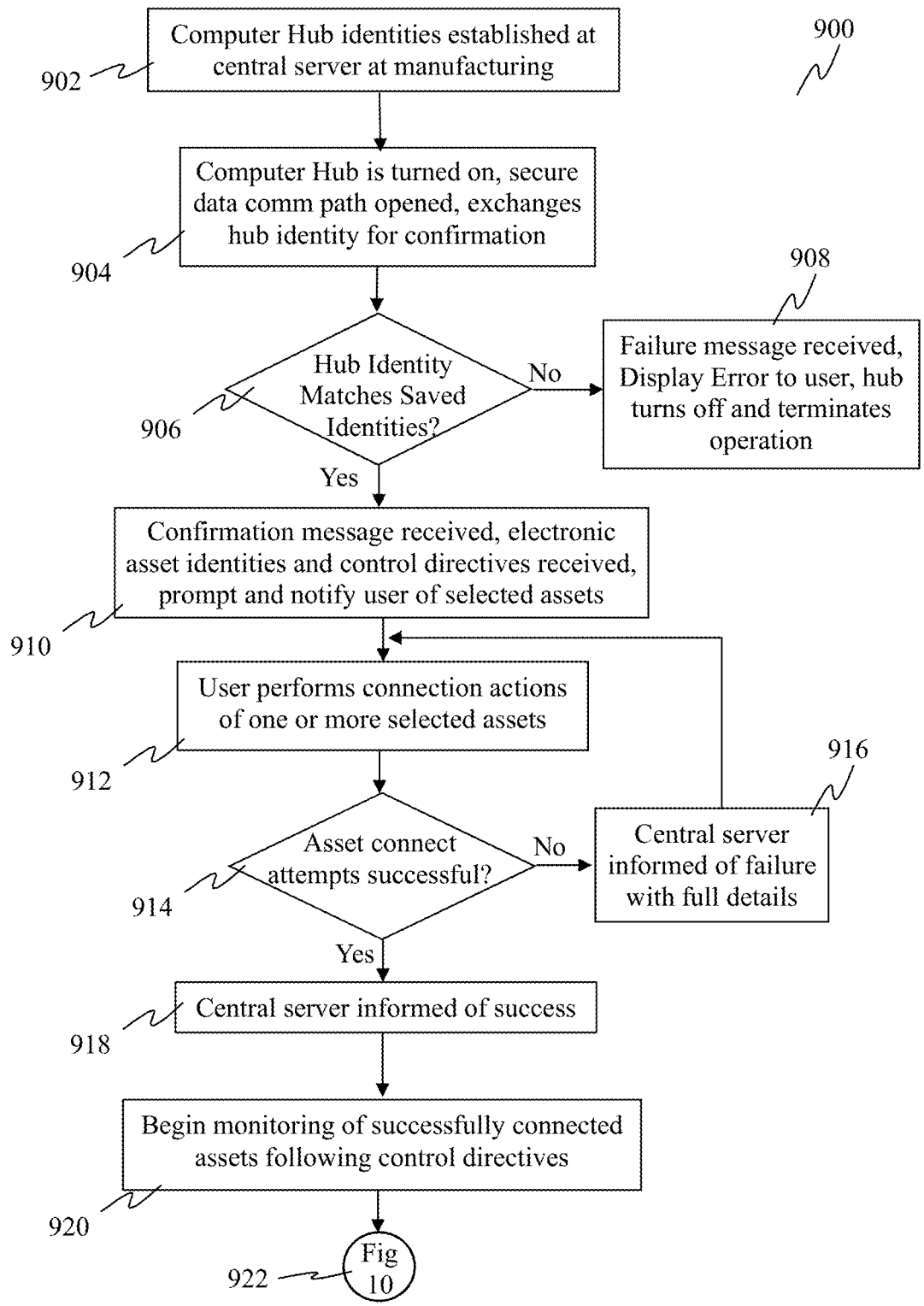
FIG. 9 shows a data flow diagram for one embodiment of the steps taken by a user at the computer hub to setup electronic assets.

FIG. 9 shows a data flow diagram 900 for one embodiment of the steps taken by a user 134, 138 at the computer hub 116, 216 to setup electronic assets 120, 220. There are many embodiments and several additional functions that could be highlighted for those embodiments. Embodiments with pill dispensing, VTOL flight and flight control, and many others that could generate additional steps not shown in this set of data flow diagrams 900.

The first step is when the computer hub 116, 216 establishes its hub identity and exchanges it with the central server 902. As discussed earlier, in one embodiment this could be a CPU based serialized and unique identification number. In other embodiments it is the exchange of a public/private encryption key pair. In other embodiments it involves receiving a unique identifier from the central server 102, 202 in a closed, private space that protects the secret value. Once exchanged the central server 102, 202 places it within the non-transient memory of its database 106, 206.

When the computer hub 116, 216 is turned on it opens a secure data path and exchanges its hub identity for confirmation 904. Even with a secure data path like secure socket layer (SSL), transport layer security (TLS) or datagram transport layer security (DTLS) the computer hub 116, 216 still needs to authenticate itself with the central server 904. This step catches any rogue computer hubs that have been built to infest or corrupt the central server 102, 202. If the hub identity does not match the saved identities 906 the computer hub 116, 216 receives a failure message from the central server 908. It displays an error to the user, the hub turns off and operations terminate 908.

If the computer hub 116, 216 does match the central server's database 906 a confirmation message is received 910. Sometime later the computer hub 116, 216 receives electronic asset 120, 220 assignment and control directive messages 910. The user is prompted, the display on the computer hub 116, 216 changes and the user can act on the changes from the central server 910.

In some embodiments depending on the computer hub 116, 216 requirements the user 134, 138 might also have to authenticate themselves before use. This might include a biometric input, a biomedical input, tapping an NFC card or lanyard or some other step to prove who they are to the computer hub 116, 216.

When required, after the user 134, 138 is authenticated they can then perform one or more actions to enable the connection of the one or more electronic assets 912. This might involve turning the electronic asset 120, 220 on, applying power to the electronic asset 120, 220, physically plugging it into the computer hub 116, 216 or many other possible steps 912.

The computer hub 116, 216 then watches for the connection and if not successful will prompt the user 134, 138 to retry 916. If the failure persists the computer hub 116, 216 might inform the central server 102, 202 that this electronic asset 120, 220 might have bigger quality issues 916. At this point that specific electronic asset 120, 220 might be retired and a new electronic asset 120, 220 provided in its place.

If the connection attempt is successful, the central server 102, 202 is informed of the success 918. The computer hub 116, 216 can then begin its monitoring of the successfully connected electronic assets 120, 220 following the control directives 920. To illustrate the process of monitoring, controlling and managing the process flow moves to FIG. 7 (922).

Figure 10:
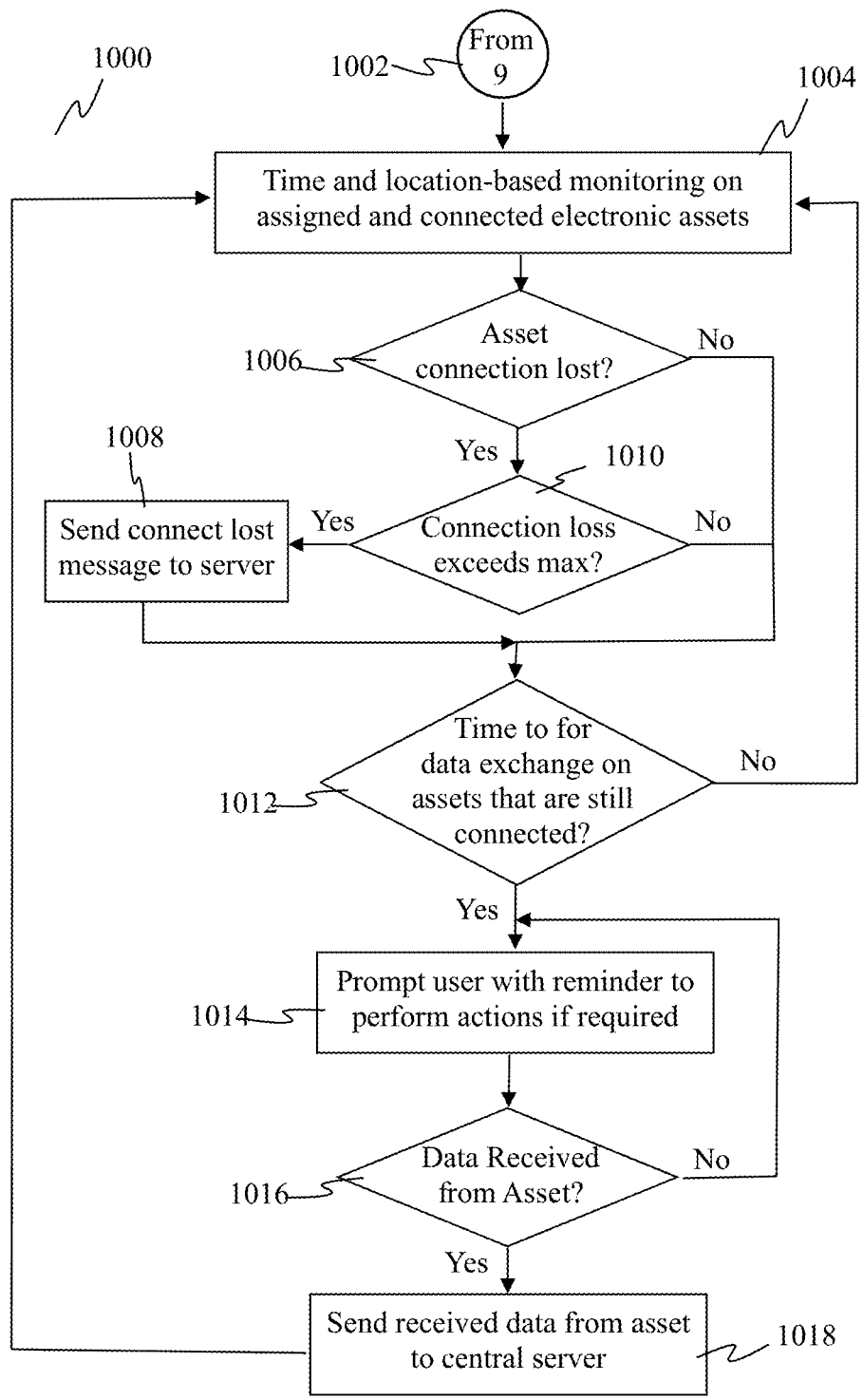
FIG. 10 shows a data flow diagram for one embodiment of the steps taken by a computer hub to manage and monitor electronic assets.

FIG. 10 shows a data flow diagram 1000 for one embodiment of the steps taken by a computer hub 116, 216 to manage and monitor electronic assets 120, 220. The process flow starts after FIG. 6 is complete and the electronic asset is connected and ready to go 1002. The first step is establishing various time and location-based monitoring parameters within the system 1004. This could involve the setup of system timers, GPS movement parameters, GEO-based tags and connection interrupt triggers 1004. In some embodiments low-level O/S interrupts are used to detect the removal of physical connectors.

If the connection has been detected as lost 1006, through the use of interrupts for example, then a further check is made to see if the disconnection time has exceeded the configured maximum connection lost time 1010. These types of control directive parameters have been previously entered by the computer hub manager 130, 230 and established for each of the electronic assets 120, 220. If the connection has been lost for a maximum period of time a connection lost message is sent to the server 1008.

If the electronic asset 120, 220 connection has not been lost and for all other connected assets a check is made to see if it is time to do a data exchange with one or more of the connected electronic assets 1012. If there are no expired timers at this time then the flow of control returns to reset timers and wait for another interrupt 1004.

If a timer has expired 1012 then the user 134, 138 might be prompted to perform an action to generate data for the central server 1014. For a patient using the computer hub 116, 216 to track vitals and health data, they might be prompted to put on a blood pressure cuff and take their blood pressure 1014. If the computer hub user 138 is a EMS driver they might be prompted to push a button on the EKG machine to send it into a diagnostic check to ensure it is still in peek operating performance 1014.

If the computer hub 116, 216 then receives data from the asset 1016 it sends the data to the central server 1018 and returns to wait on other interrupts 1004. If there is no data received from any of the electronic assets 120, 220 the flow returns back to re-prompt the user to perform the necessary action to generate the data necessary 1014. This can continue for an extended period of time until the user 134, 138 complies with the action.

Figure 11:
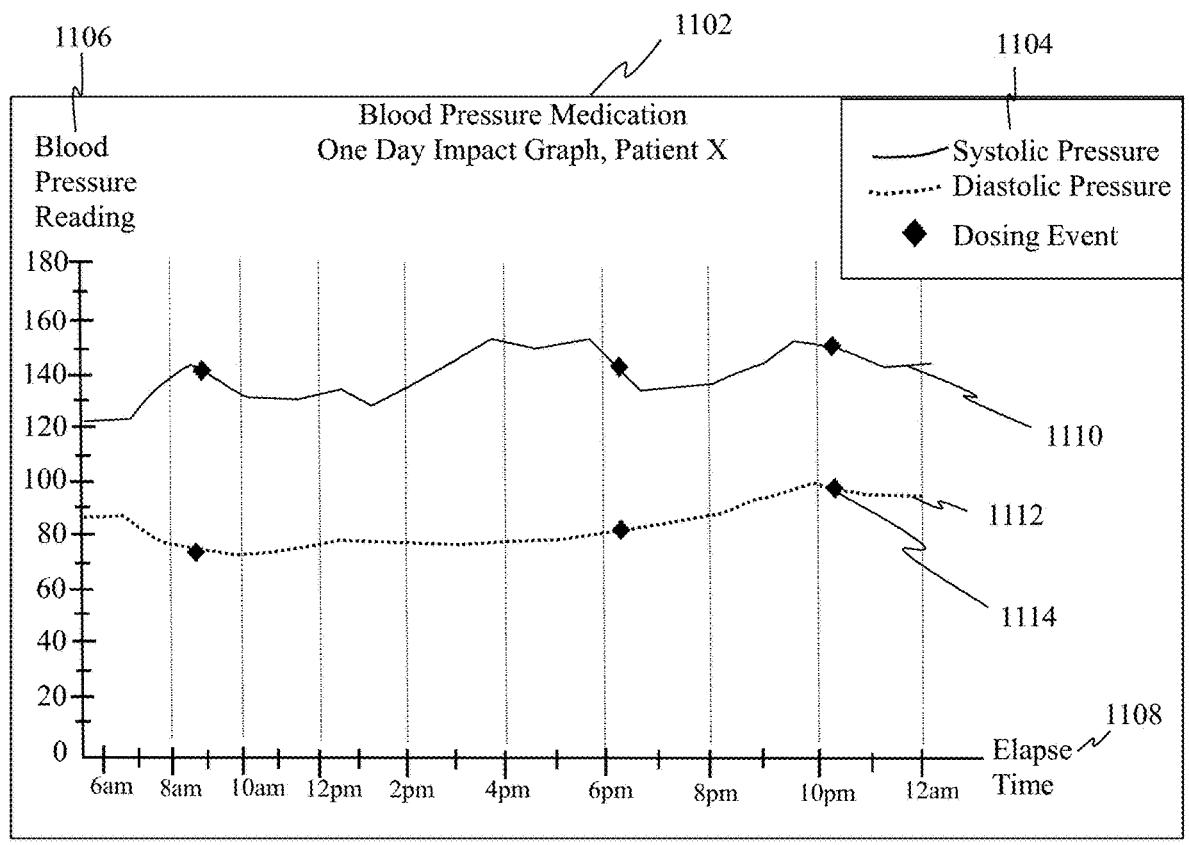
FIG. 11 shows an embodiment for an example impact graph charting the daily information received from computer hubs and one or more electronic assets.

Turning to FIG. 11 there is provided one embodiment for an impact graph 1102 charting the daily information received from computer hubs 116, 216 and one or more electronic assets 120, 220. The embodiment shown illustrates information about the one-day impacts of blood pressure medication on Patient X 1102. There are many other potential embodiments for this information presentation. In some embodiments the information is related to blood glucose and the impacts of injecting insulin. In another embodiment it could be the impact of vehicle location, movement, and the loss of battery power. In some embodiments the computer hub 116 is performing trackable information that is also graphed, for example it could be dispensing medication as shown in FIG. 11.

In other embodiments the information is coming only from the electronic assets 120, 220. For example, readings from a glucose blood sugar monitor and injection results from an insulin pen could be graphed showing the hourly impact of insulin injection on the blood sugar of a patient. Both readings are given to the computer hub 116, 216 from a different electronic asset 120, 220 to be relayed to the central server 102, 202 for correlation and graphical presentation.

Additionally, a glucose insulin chart could be provided to the computer hub 120 and when a glucose reading comes in from a Bluetooth connected glucose monitor the information could be displayed graphically to the patient 134 to guide them to the exact level of insulin they need to take, if any, at that time.

A similar charting operation could be performed when a blood pressure reading is taken just before taking a blood pressure pill to lower your blood pressure level. If a patient's 134 blood pressure reading shown graphically on the computer hub 120 from the connected Bluetooth blood pressure cuff shows a lower than expected blood pressure reading, the patient might be directed to not take that pill or the pill will not even be ejected from the drug dispensing computer hub 120.

In other embodiments different graphing methods could be used. For example, each discrete blood pressure reading 1106 could be shown as a bar and a time based 1108 bar diagram could have been used.

In this illustration the blood pressure medication graph 1102 provides a legend charting systolic and diastolic pressure with additional data points for dosing events 1104. On one axis is the blood pressure readings 1106, mapped over a period of time 1108 representing approximately one day. Based on the previous figures the information collected has been from Patient X 1102 who has been prompted by their computer hub 116, 216 to perform blood pressure readings about every 30 to 60 minutes throughout the day. It is expected that patient X is busy and provides a best effort at the necessary readings.

The systolic pressure readings are shown with a solid line 1110 and throughout the line are periods in the day when Patient X has a dosing event 1114. Similarly, the diastolic pressure readings are shown with a dotted line 1112 and throughout the line the same dosing events 1114 are shown when they take place throughout the day. As with any blood pressure, throughout the day the patient's blood pressure rises and taking their medication helps to bring down their pressure readings.

For a trained professional looking at this information many things could be understood. For example, it might be possible to determine that Patient X is clearly taking their afternoon drug dose too late in the day. It appears Patient X's blood pressure starts to claim around 4 pm, but it is not until 6 pm they take their dinner time dose of medication. It is likely that Patient X feels lightheaded and tired from 4 pm to 6 pm. By reviewing several weeks of data, a trained doctor might then be able to suggest to Patient X that moving their drug dosing time to 4 pm from 6 pm would be very beneficial to them and provide a better quality of life.

Complex impact charts like this, about a wide range of vitals and other information, can be reviewed and interpreted by trained professionals to produce tangible improvements for the users of computer hubs 116, 216 and electronic assets 120, 220.

Figure 12:
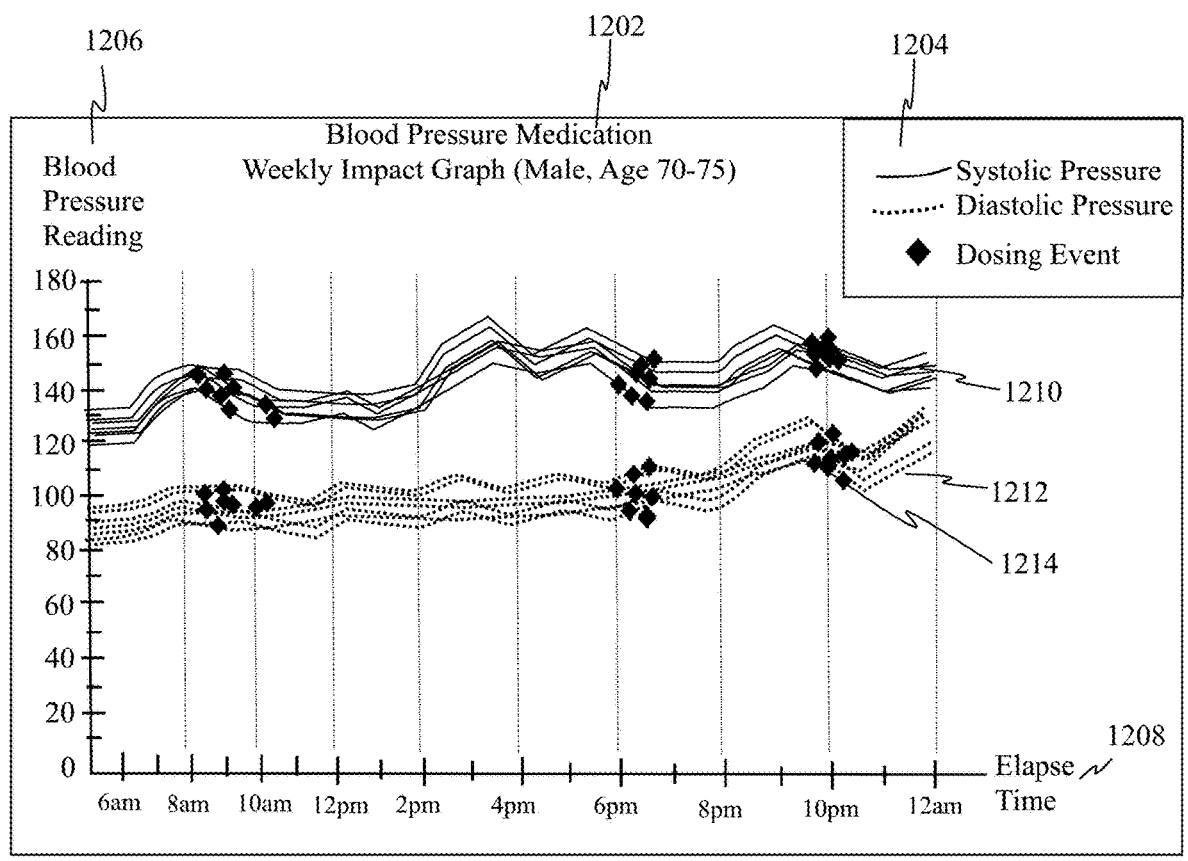
FIG. 12 shows another embodiment for another example impact graph charting the weekly information received from a computer hub and one or more electronic assets.

Turning to FIG. 12 there is provided another embodiment for an impact graph 1202 charting the weekly information received from a computer hub 116, 216 and one or more electronic assets 120, 220. There are many possible embodiments for illustrating and using this type of received information from a computer hub 116, 216. In some embodiments the information can be anonymized, as shown in FIG. 12. In other embodiments the information might be amalgamated for a single patient over a week, month or several months to see repeating patterns in one person's vitals.

In those embodiments where the information is amalgamated from one patient, the information is targeted only at that person's body, daily choices, activities, food consumption and lifestyle. In those embodiments where the information is anonymized, the information can point toward trends in a broad population. In FIG. 12 for example the blood pressure medication impact graph is for males, from age 70 to age 75 (1202). Looking at a segment of the population over a week, month or even a year can point towards treatments for those patients dealing with blood pressure issues and health conditions like coronary heart disease (CHD).

FIG. 12 provides information on systolic pressure, diastolic pressure and dosing events 1204 across the full population that has been selected for this graph. The first axis is the blood pressure reading 1206 and the second axis is the elapse time 1208 in a day when blood pressure readings were taken, and drugs were ingested. The graph provides a visual for the systolic pressure shown with a solid line 1210 and the impact of various medication dosing events 1214 taken throughout the day. Similarly, the graph provides a visual for the diastolic pressure shown with a dotted line 1212 and the impact of the same medication events on the patient's diastolic blood pressure.

For a trained professional this type of anonymized information can guide drug rehabilitation therapies, drug consumption times, drug type selections based on a patient age or gender and many other useful decision factors. Knowing how different physiologies perform based on a person's age and how a heart degenerates in different populations, can inform the entire health community with respect to how to treat these different populations. Such information could be invaluable in many different health fields like diabetes, chronic obstructive pulmonary disease (COPD), obesity and others could all benefit from anonymized data as illustrated in FIG. 12.

Moving towards the collection and correlation of this information across populations of millions would allow advanced computer analysis to be performed on the data. This form of 'big data' leads to potential for artificial intelligence algorithms targeted at using statistical analysis methods to find reoccurring patterns in the data set. For example, locating patterns and providing insights to professionals dealing with common illnesses in North America could help in the battle against many chronic conditions.

Using the system to collect both medication consumption information and vital readings from hundreds and thousands of patients would allow a computer algorithm to provide insights like a person of this gender and this age with blocked arteries is likely to require these medications prescribed and they should be taken at these time periods for optimal benefit and performance. Taking some of the guess work out of medication prescriptions and dosing times could lead to reduced healthcare costs across North America.

The invention claimed is:

1. A method of securely communicating with one or more electronic assets using an authenticated computer hub and a central server, the method comprising:
   at a central server,
      establishing a secure communication channel between the central server and a computer hub to receive a hub identity uniquely identifying the computer hub;
      creating an authenticated computer hub by matching the received hub identity against a database of authenticated computer hubs and transmitting an identity confirmation message;
      providing a hub manager interface to the authenticated computer hub, the computer hub manager interface for selecting and assigning one or more electronic assets and control directives defining operational usage parameters for selected and assigned electronic assets within an asset database, and securely transmitting identities of the selected and assigned electronic assets and control directives to the authenticated computer hub;
      receiving connection results and communication results from the authenticated computer hub when received from the selected and assigned electronic assets following the control directives provided by the hub manager interface;
   at the authenticated computer hub,
      communicating over the secure communication channel the hub identity for verification at the central server in order to receive the identity confirmation from the central server;
      receiving instructions providing identifiers for the selected and assigned electronic asset that are to be granted access to the authenticated computer hub from the central server;

providing a user interface indicating that the selected and assigned electronic assets have been granted access;

connecting to the selected and assigned electronic assets through a short-range network and communication method providing two-way communication between the selected and assigned electronic assets and the authenticated computer hub;

transmitting results of the connection attempt to the central server;

executing the control directives to periodically attempt to communicate with the selected and assigned electronic assets to exchange data, and communicating over the network connection the communication results from the one or more authorized electronic assets using guidelines provided within the control directives.

2. A method of claim 1 wherein the short-range communication method is a Bluetooth short-range communication method, and wherein the secure communication channel uses a long-range communication method comprising an IoT long-range cellular communication method.

3. A method of claim 1 wherein the communication results comprise failure to communicate with one or more of the selected and assigned electronic assets.

4. A method of claim 1 further comprising verifying a user operating the user interface in order to couple with one or more authorized electronic assets through one or more authentication process, wherein the authentication process comprises verifying a user using at least one of a biometric input to authenticate, and a near-field communication (NFC) input.

5. The computer method of claim 1 further comprising, at the authenticated computer hub, continuously monitoring the status of the connection to the one or more electronic assets.

6. The computer method of claim 1 further comprising, prior to providing the user interface, receiving a biometric confirmation for the authenticated computer hub, and using the biometric confirmation to identify who collected data from an electronic asset associated with the authenticated computer hub after receiving the biometric confirmation.

7. The computer method of claim 1 further comprising associating an electronic asset to another physical object to generate an authorized electronic asset.

8. The computer method of claim 1 further comprising displaying, using the control directives, visualizations of data corresponding to readings received from one or more assets.

9. The computer method of claim 1 further comprising, at the authenticated computer hub, receiving a message from a first electronic asset and sending a control message to a second electronic asset based on a value extracted from the first message.

10. The method of claim 1 further comprising anonymizing the communication results from the authenticated computer hub and one or more authorized electronic assets using with an artificial intelligence process to produce statistically useful patterns within the data set.

11. A system for securely communicating with one or more electronic assets to using an authenticated computer hub and a central server, the system comprising:

an authenticated computer hub comprising:
a communication device for transmitting a hub identity uniquely identifying the computer hub and communication results received from one or more authenticated electronic assets to a central server, and for receiving an identity confirmation message and electronic asset identities to be authorized with control directives defining operational usage parameters;

a user interface to display that one or more electronic assets have been granted access and to connect to one or more authorized electronic assets;

a short-range communication device to enable a user to connect to one or more electronic assets and to communicate with the one or more authorized electronic assets to exchange information based on control directives;

the central server comprising:
a non-transitory memory storing a list of authenticated hub identities, one or more identifiers for electronic assets, control directives, and a received communication results from the one or more authorized electronic assets;

a hub manager interface for selecting the authenticated computer hub and defining electronic assets and control directives for connecting to the authenticated computer hub;

a communication interface for:
receiving hub identity requests, connection results from attempts to connect authorized electronic assets and communication results from attempts to communicate with authorized electronic assets;

transmitting a hub identity confirmation message, one or more authorized electronic asset identities and control directives defining operational usage parameters of those devices;

a hardware processor for:
computing matching results of received hub identities against known hub identities to create authorized hub identities;

determining additional actions based on connection results from connection attempts made with one or more authorized electronic assets and communication results from attempts to communicate with the one or more electronic assets, and building communication charts based on information received from the one or more devices via the authorized computer showing the time each communication attempt was performed and the results.

12. The computer system of claim 11 wherein the authenticated computer hub is a medical device that generates patient medical data while supporting the authorizing electronic assets.

13. The computer system of claim 11 wherein the authenticated computer hub is dedicated to watching the status of the connection to one or more electronic assets.

14. The computer system of claim 11 wherein the user interface requires a biometric confirmation before the computer hub can be used, wherein the biometric confirmation is used to identify who collected data from an electronic asset associated with the computer hub after biometric confirmation.

15. The computer system of claim 11 wherein the electronic asset is associated to another physical object enabling it to become an authorized electronic asset.

16. The computer system of claim 11 wherein the computer hub can receive a message from one electronic asset and send a control message to a second electronic asset based on the value found within the first message.

17. The computer system of claim 11 wherein the short-range communication method is a Bluetooth short-range communication method, and wherein the long-range communication method is an IoT long-range cellular communication method.

18. The computer system of claim 11 wherein the communication results can include the failure to communicate with one or more of the authorized electronic assets.

19. The computer system of claim 11 wherein the authenticated computer hub is dedicated to watching the status of the connection to one or more electronic assets.

20. The system of claim 11 wherein the communication results from a computer hub and one or more authorized electronic assets is anonymized and used with an artificial intelligence process to produce statistically useful patterns within the data set.

* * * * *